US 9,408,553 B2

(12) United States Patent
Hamaguchi et al.

(10) Patent No.: US 9,408,553 B2
(45) Date of Patent: Aug. 9, 2016

(54) FAT MASS MEASUREMENT APPARATUS

(71) Applicants: Takehiro Hamaguchi, Kyoto (JP); Hiromichi Karo, Kyoto (JP); Kazuhisa Tanabe, Kyoto (JP); Yasuaki Murakawa, Kyoto (JP)

(72) Inventors: Takehiro Hamaguchi, Kyoto (JP); Hiromichi Karo, Kyoto (JP); Kazuhisa Tanabe, Kyoto (JP); Yasuaki Murakawa, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 910 days.

(21) Appl. No.: 13/712,140

(22) Filed: Dec. 12, 2012

(65) Prior Publication Data
US 2013/0102873 A1    Apr. 25, 2013

Related U.S. Application Data

(63) Continuation of application No. PCT/JP2011/063647, filed on Jun. 15, 2011.

(30) Foreign Application Priority Data

Jul. 22, 2010    (JP) .................................. 2010-164627

(51) Int. Cl.
*A61B 5/053*    (2006.01)
*A61B 5/00*    (2006.01)

(52) U.S. Cl.
CPC .............. *A61B 5/0537* (2013.01); *A61B 5/4872* (2013.01); *A61B 5/7278* (2013.01); *A61B 5/6823* (2013.01); *A61B 5/704* (2013.01); *A61B 2562/046* (2013.01)

(58) Field of Classification Search
CPC .. A61B 5/0537; A61B 5/4872; A61B 5/7278; A61B 5/6823; A61B 5/704; A61B 2562/046
See application file for complete search history.

(56) References Cited

U.S. PATENT DOCUMENTS

2004/0059242 A1*    3/2004    Masuo et al. .................. 600/547
2004/0111045 A1*    6/2004    Sullivan et al. ............... 600/595

(Continued)

FOREIGN PATENT DOCUMENTS

CN    1146329 A    4/1997
CN    1891147 A    1/2007

(Continued)

OTHER PUBLICATIONS

International Search Report issued in corresponding International Application No. PCT/JP2011/063647 dated Sep. 6, 2011 and English translation thereof (2 pages).

(Continued)

*Primary Examiner* — Rene Towa
(74) *Attorney, Agent, or Firm* — Osha Liang LLP

(57) ABSTRACT

A fat mass measurement apparatus includes an area detection unit that detects a predetermined position in a measurement subject's trunk area and detecting a predetermined area in the trunk area using the detected position; an electrode position setting unit that sets, on the body surface at the predetermined area detected by the area detection unit, a plurality of positions along the vertical direction of the trunk area for measuring the body impedance; an impedance measurement unit that measures the body impedance by bringing the impedance measurement electrodes into contact with each of the plurality of positions that have been set; and an abdominal area fat mass calculation unit that calculates a fat volume at the predetermined area based on the body impedances at each of the plurality of positions measured by the impedance measurement and the size of the trunk area at the predetermined area.

5 Claims, 14 Drawing Sheets

(56) References Cited

U.S. PATENT DOCUMENTS

| | | | |
|---|---|---|---|
| 2008/0243026 A1* | 10/2008 | Tsuji | 600/547 |
| 2011/0137199 A1* | 6/2011 | Karo et al. | 600/547 |
| 2012/0041344 A1* | 2/2012 | Flodmark | 600/587 |

FOREIGN PATENT DOCUMENTS

| | | | |
|---|---|---|---|
| CN | 101112310 A | | 1/2008 |
| JP | 11-113870 A | | 4/1999 |
| JP | 2000-175875 A | | 6/2000 |
| JP | 2005-288023 A | | 10/2005 |
| JP | 2009-022515 A | | 2/2009 |
| JP | WO 2010/032835 | * | 3/2010 |
| JP | 2010-069248 A | | 4/2010 |
| WO | 2010/032837 A1 | | 3/2010 |

OTHER PUBLICATIONS

Patent Abstracts of Japan, Publication No. 11-113870, Published on Apr. 27, 1999, 1 page.
Patent Abstracts of Japan, Publication No. 2005-288023, Published on Oct. 20, 2005, 1 page.
Patent Abstracts of Japan, Publication No. 2010-069248, Published on Apr. 2, 2010, 1 page.
Patent Abstracts of Japan, Publication No. 2000-175875, Published on Jun. 27, 2000, 1 page.
Patent Abstracts of Japan, Publication No. 2009-022515, Published on Feb. 5, 2009, 1 page.
Office Action issued in corresponding Chinese Application No. 201180035646.8 dated Aug. 11, 2014, and English translation thereof (14 pages).

* cited by examiner

FAT MASS MEASUREMENT APPARATUS

TECHNICAL FIELD

This invention relates to fat mass measurement apparatuses, and particularly relates to fat mass measurement apparatuses that measure a fat mass in an abdominal area of a measurement subject.

BACKGROUND ART

A body fat measurement apparatus that uses an impedance measured between multiple electrodes affixed to measurement areas of a body to calculate a body fat distribution across a cross-section of the areas where the electrodes are affixed has been disclosed in, for example, Patent Literature 1 (JP H11-113870A) and Patent Literature 2 (JP 2005-288023A).

SUMMARY OF INVENTION

To accurately diagnose endocrine/metabolic system-related risks, it is desirable to measure a fat mass, and more specifically, to measure the volume of fat in the abdominal area. However, although body fat measurement apparatuses disclosed in Patent Literature 1 (JP H11-113870A) and Patent Literature 2 (JP 2005-288023A) do calculate a body fat distribution across a cross-section of the areas where the electrodes are affixed, these apparatuses do not calculate the volume.

Measurement that uses a tomographic image of the abdominal area obtained through X-ray CT (computed tomography) exists as another conventional method for measuring the fat volume in the abdominal area. In this method, tomographic images of the abdominal area are captured in multiple areas, and the area of the fat in the image is geometrically calculated from the respective multiple abdominal area tomographic images, after which the calculated areas are integrated to obtain a fat mass (volume); the measurement has thus taken a long time.

It is also possible to capture the same type of tomographic images of the abdominal area as X-ray CT using MRI (magnetic resonance imaging), but measurement of a fat mass (volume) takes a long time in this case as well. Moreover, oversized equipment is necessary when using X-ray CT or MRI, and thus such methods are inefficient.

Therefore, one or more embodiments of the present invention provide a fat mass measurement apparatus capable of efficiently measuring a fat mass at a predetermined area of a body.

A fat mass measurement apparatus according to one or more embodiments of the present invention is an apparatus that measures a fat mass in a body based on a body impedance measured by bringing impedance measurement electrodes into contact with a measurement subject's body surface.

According to one or more embodiments of the present invention, the fat mass measurement apparatus includes: a position detection unit for detecting a predetermined position in a trunk area of the measurement subject; an area detection unit for detecting a predetermined area in the trunk area using the position detected by the position detection unit; an electrode position setting unit for setting, on the body surface at the predetermined area detected by the area detection unit, a plurality of positions along the vertical direction of the trunk area for measuring the body impedance; an impedance measurement unit that measures the body impedance by bringing the impedance measurement electrodes into contact with each of the plurality of positions set by the electrode position setting unit; and a fat mass calculation unit for calculating a fat mass of the predetermined area based on the body impedances at each of the plurality of positions measured by the impedance measurement unit and the size of the trunk area at the predetermined area.

According to one or more embodiments of the present invention, a fat mass at a predetermined area can be measured efficiently.

DETAILED DESCRIPTION OF INVENTION

Figure 1:
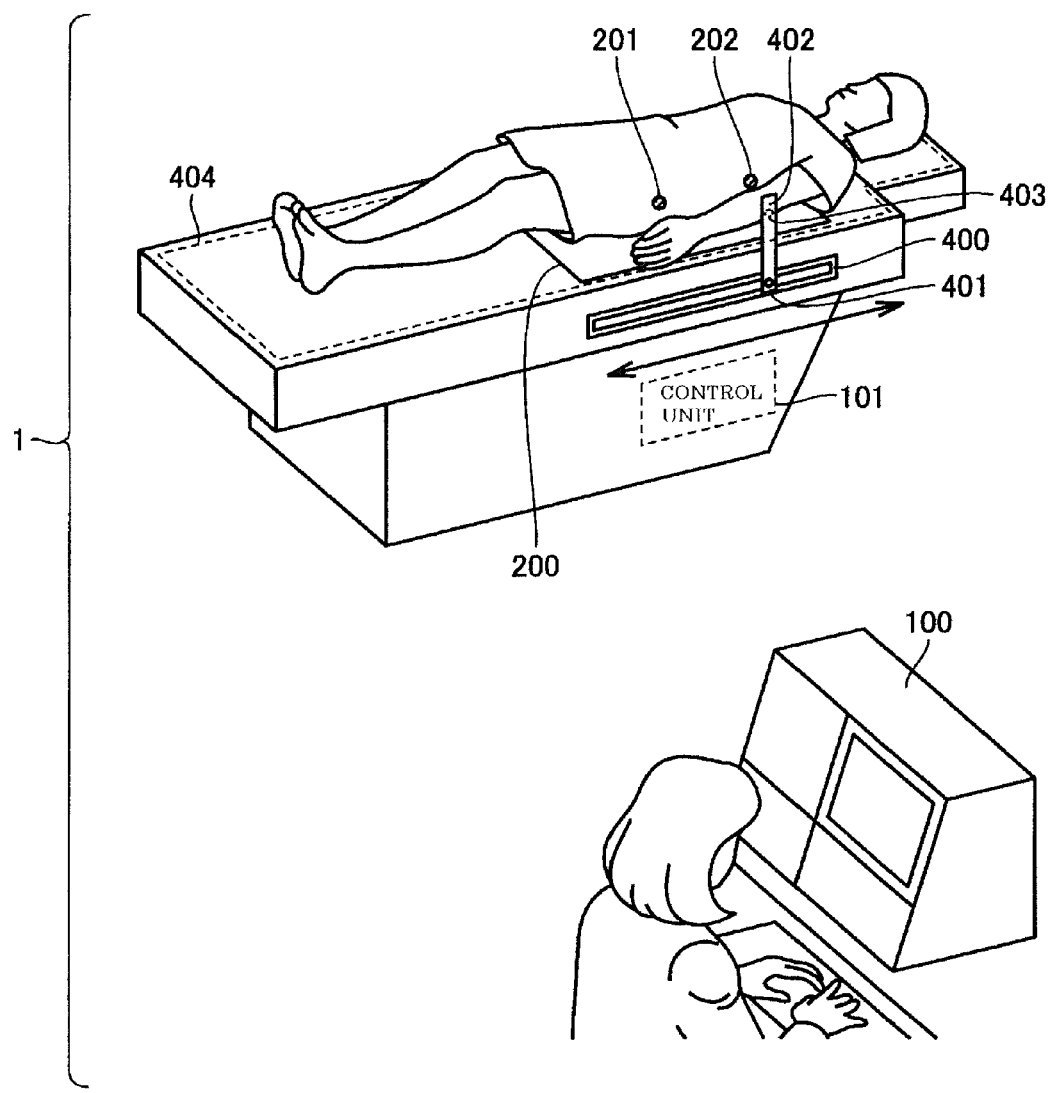
FIG. 1 is an external view of a fat mass measurement apparatus according to a first embodiment of the present invention.

Embodiments of the present invention will be described in detail hereinafter with reference to the drawings. Note that identical or corresponding areas of the drawings will be assigned the same reference numerals, and descriptions thereof will not be repeated.

In the embodiments, "trunk area" refers to the trunk portion of a body. "Abdominal area" refers to the trunk area aside from the chest area, and serves as an abdominal area fat mass measurement area. In the embodiments, the abdominal area fat mass measurement area refers to an area from the twelfth rib to the ilium. An "area distanced from the abdominal area" includes the upper limbs, consisting of the upper arms, forearms, wrists, and fingers, and the lower limbs, consisting of the thighs, calves, ankles, and toes. "Body axis" refers to an axis located along the direction approximately perpendicular to the side cross-section of a measurement subject's abdominal area. The "abdominal area front surface" includes the areas of the measurement subject's abdominal area that are visible when the measurement subject is viewed from the front. For example, this includes the areas of the measurement subject's abdominal area that are visible when the measurement subject is viewed from the side of his/her navel along an axis that passes through the measurement subject's navel and spine and is perpendicular to the measurement subject's body axis. The "abdominal area rear surface", meanwhile, includes the areas of the measurement subject's abdominal area that are visible when the measurement subject is viewed from the rear. For example, this includes the areas of the measurement subject's abdominal area that are visible when the measurement subject is viewed from the side of his/her spine along an axis that passes through the measurement subject's navel and spine and is perpendicular to the measurement subject's body axis.

First Embodiment

An external view of a fat mass measurement apparatus according to a first embodiment of the present invention will be described with reference to FIG. 1. As shown in FIG. 1, a fat mass measurement apparatus 1 according to the present embodiment includes a computer 100 and a control unit 101 that is communicatively connected to the computer 100. The control unit 101 is installed in a bed on which a measurement subject lies face-up. The surface size of the bed on which the measurement subject lies face-up is a sufficiently large size, and assumes that the body of the measurement subject who is lying face-up will not extend over the edges of the bed. An electrode mat 200 is disposed and anchored on the bed in a position that corresponds to the back of the measurement subject who is lying face-up.

Note that in FIG. 1, the measurement subject's clothing is designed so that there is no cloth on the abdominal area rear surface. Accordingly, the electrode mat 200 can make contact with the body surface on the abdominal area rear surface when the measurement subject is lying face-up as shown in FIG. 1.

The electrode mat 200 is approximately rectangular in shape; the direction in which the long side of the electrode mat 200 extends matches the direction in which the body axis of the measurement subject extends upon the bed (that is, the lengthwise direction of the bed), whereas the short side extends along a direction approximately orthogonal to the body axis of the measurement subject upon the bed. The length of the short side matches the length of the bed in the widthwise direction thereof.

A slide rail 400 that extends along the lengthwise direction of the bed is formed on a side surface in the lengthwise direction of the bed. The length of the slide rail 400 matches the length of the long side of the electrode mat 200.

A slider 401 is embedded in the slide rail 400 so as to be capable of freely moving along the rail. One end of a slide bar 402 that extends in the direction orthogonal to the slide rail 400 is connected and anchored to the slider 401. Accordingly, when the slider 401 slides along the slide rail 400, the slide bar 402 moves freely along the slide rail 400, or in other words, along the long side of the electrode mat 200.

An area where the slider 401 is attached to the rail is connected to a rotating shaft of a stepping motor (not shown) of the control unit 101. Accordingly, the slider 401 slides in a direction and at a distance based on the rotation direction and rotation angle (also called "rotational amount" hereinafter) of the stepping motor, in tandem with the rotation of the stepping motor. As a result, the position of the slide bar 402 along the slide rail 400 can be detected based on the rotational amount of the stepping motor.

Position Detection Function and Predetermined Area Detection Function

Marks 201 and 202, configured of adhesive sheets, are applied to predetermined positions on the side surface or front surface of the trunk area of the measurement subject who is lying on the bed face-up.

A laser sensor 403 capable of emitting laser light toward the measurement subject who is lying face-up is attached to the opposite side of the slide bar 402 as the side connected to the slider 401. The marks 201 and 202 are configured of a material that reflects the laser light emitted from the laser sensor 403.

During operations, the laser sensor 403 emits laser light while the slide bar 402 slides along the slide rail 400. When the slide bar 402 moves and reaches positions on the slide rail 400 that correspond to the marks 201 and 202, the emitted laser light is reflected by the marks 201 and 202. The reflected light is received by a light-receiving portion of the laser sensor 403. The laser sensor 403 outputs a light-received signal when the light reflected by the marks 201 and 202 has been received. Accordingly, the positions of the slide bar 402 on the slide rail 400 when the light-received signal is detected corresponds to the positions of the marks 201 and 202 along the long side of the electrode mat 200.

Here, the marks 201 and 202 are applied to predetermined areas of the trunk area for measuring an abdominal area fat mass, and more specifically, are applied to the vicinity of the twelfth rib and the ilium, respectively, which serve as indicators for areas in the abdominal area. Accordingly, the positions of predetermined areas of the trunk area (that is, the abdominal area) on the electrode mat 200 can be detected based on corresponding positions of the marks 201 and 202 along the long side of the electrode mat 200 detected when the light-received signal is outputted from the laser sensor 403.

Here, detecting the position of a predetermined area of the trunk area on the electrode mat 200 is referred to as "detecting a predetermined area".

Note that the marks 201 and 202 may be affixed to the trunk area using a gel, a belt, or the like, instead of an adhesive sheet.

Furthermore, although both the marks 201 and 202 are described as being affixed, it is acceptable to affix only one of the marks 201 and 202. In other words, depending on the height of the measurement subject, the positions of the twelfth rib and the ilium can generally be uniquely specified, and thus one of those positions may be detected based on the light-received signal from the laser sensor 403, and the other position may then be detected based on the stated detected position and the height of the measurement subject.

In this manner, predetermined positions indicated by the marks 201 and 202 can be detected using the laser sensor 403. Moreover, a predetermined area of the trunk area for which the abdominal area fat mass is to be measured can be detected based on the result of detecting the predetermined positions.

Electrode Position Setting Function

Multiple positions along the vertical direction of the trunk area (that is, the direction in which the body axis extends) for measuring an impedance are set on the surface of the body at the predetermined area. To rephrase, the electrodes of the electrode mat 200 that can make contact with the abdominal area rear surface and are to be used in the impedance measurement are determined.

Figure 2:
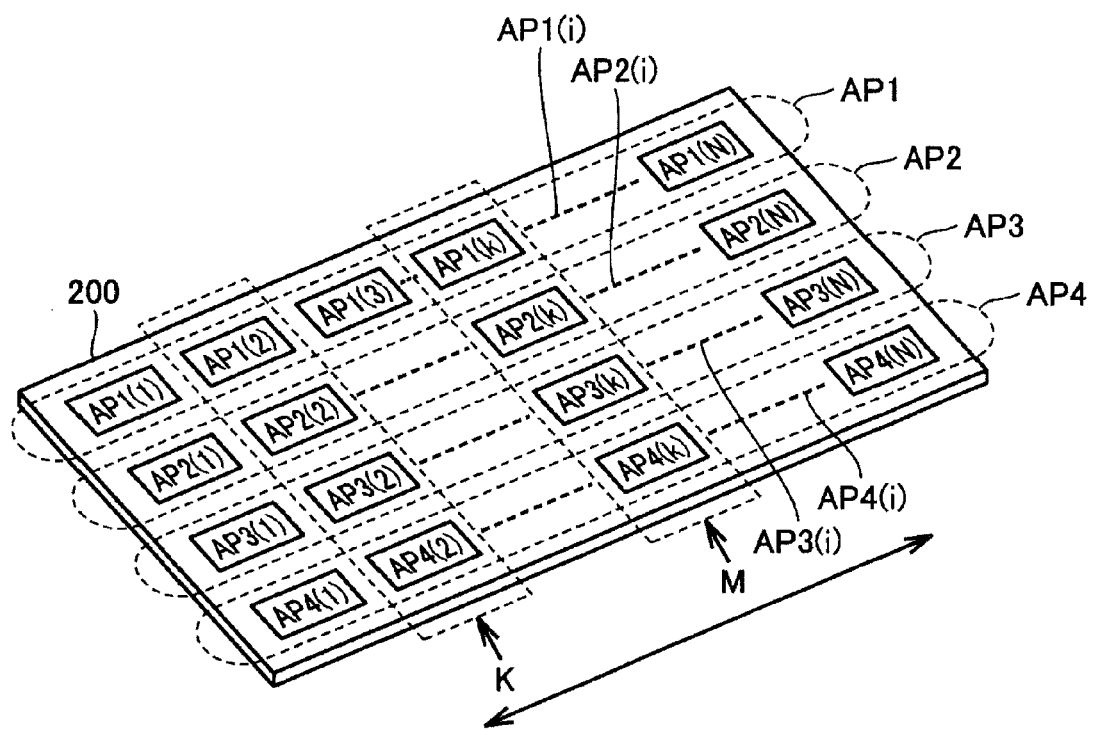
FIG. 2 is an external view of an electrode mat according to the first embodiment of the present invention.

The electrode mat 200 will be described with reference to FIG. 2. As shown in FIG. 2, in the electrode mat 200, multiple electrode pairs AP1(i), AP2(i), AP3(i), and AP4(i) (where i=1, 2, . . . , k, . . . , N) are arranged in a two-dimensional matrix. The array includes electrode pair rows AP1, AP2, AP3, and AP4 that are parallel to the long side of the electrode mat 200. The multiple electrode pairs AP1(i) are arranged in the row AP1, and in the same manner, the multiple electrode pairs AP2(i), AP3(i), and AP4(i) are arranged in the rows AP2, AP3, and AP4, respectively.

Here, the four electrode pairs arranged parallel to the short side of the electrode mat 200, or in other words, arranged adjacent to each other in the column direction (the four electrode pairs enclosed by the rectangular broken lines in FIG. 2) are called "electrode groups".

Furthermore, because the electrode pairs are in a two-dimensional array in the electrode mat 200, assuming that the short side of the electrode mat 200 corresponds to a Y axis and the long side to an X axis, the location of each electrode pair on the electrode mat 200 can be uniquely specified by coordinates (x, y).

Note that in order to simplify the descriptions, it is assumed that the length of the measurement subject's trunk area, including the abdominal area, in the direction orthogonal to the body axis matches the length of the short side of the electrode mat 200.

Next, the selection of multiple electrode pairs positioned along the vertical direction of the predetermined area in the trunk area (that is, the abdominal area) will be described. The vertical length, or in other words, the length in the direction of the body axis of the detected predetermined area is assumed to correspond to the length from positions K to M (see FIG. 2) on the long side of the electrode mat 200. In this case, of the multiple electrode groups in the electrode mat 200, multiple columns of electrode groups located in positions corresponding to the positions K to M are set as impedance measurement electrodes.

During impedance measurement, the multiple electrode groups that have been set are selected in order, and an impedance is calculated for each of the selected electrode groups using that electrode group.

Functional Configuration of Fat Mass Measurement Apparatus 1

Figure 3A:
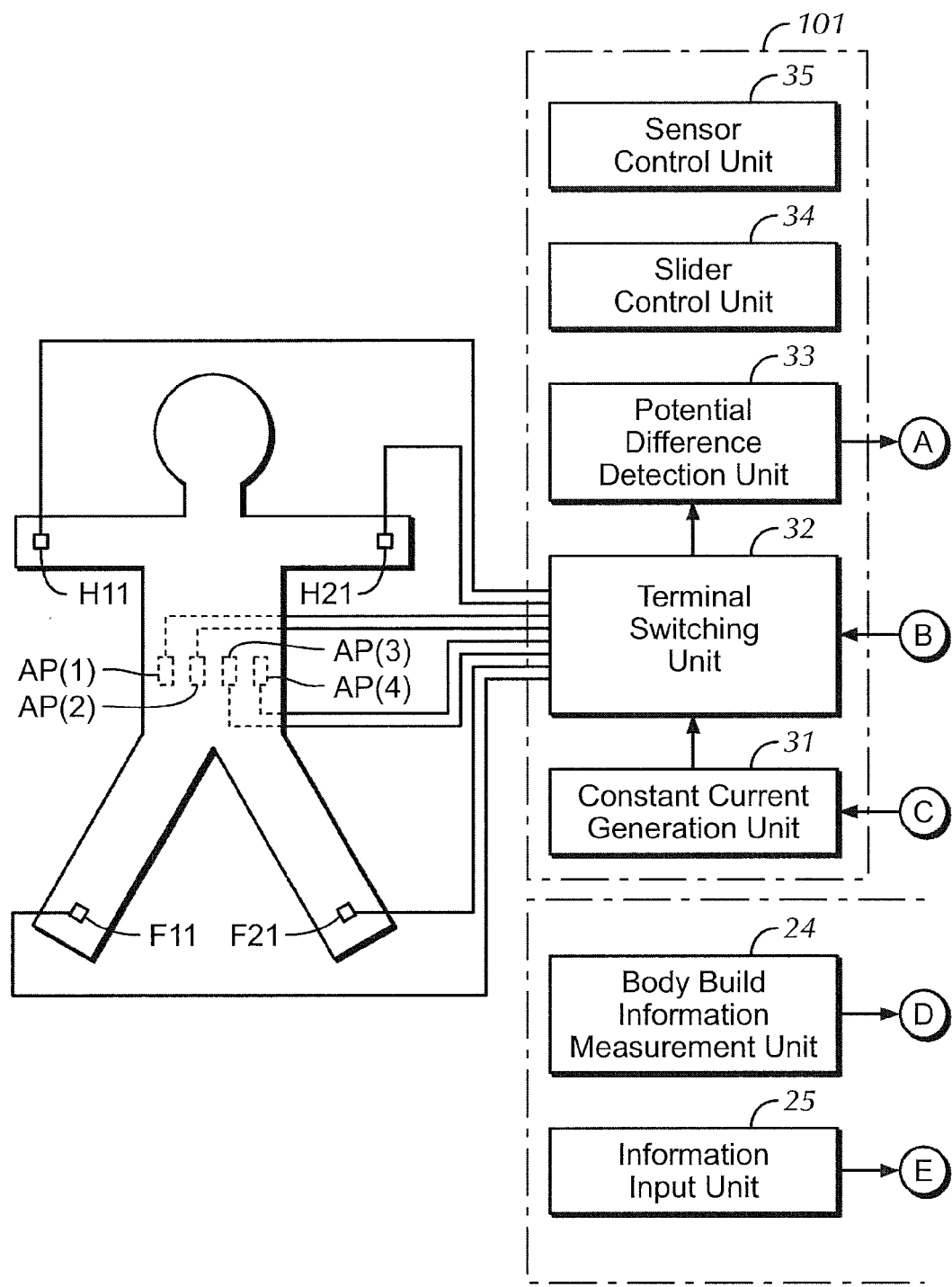
FIGS. 3A and 3B are diagrams illustrating a functional configuration of the fat mass measurement apparatus according to a first embodiment of the present invention.
Figure 3B:
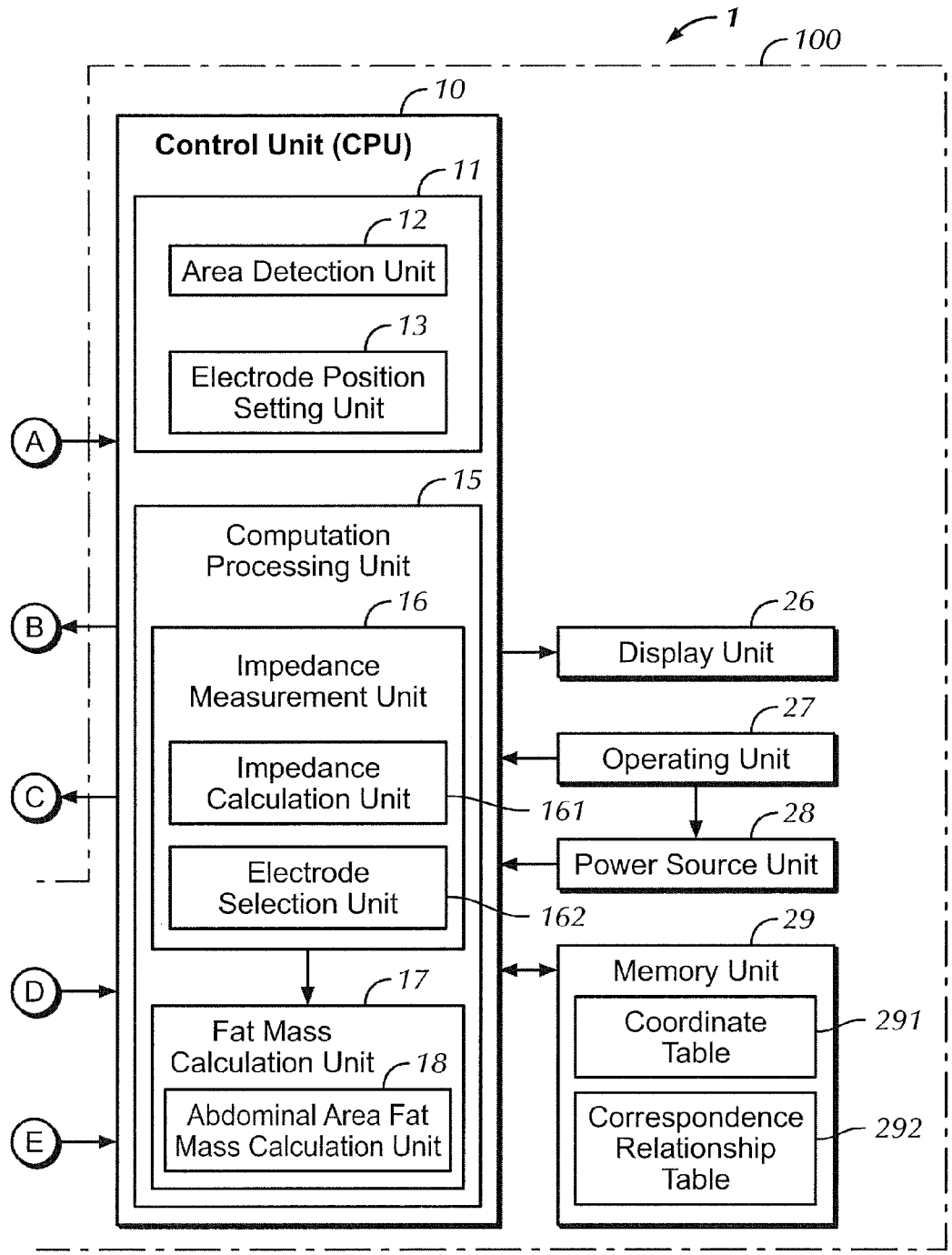

FIGS. 3A and 3B illustrate the functional configuration of the fat mass measurement apparatus 1. The control unit 101 installed in the bed includes a constant current generation unit 31 for applying a constant current to the impedance measurement electrodes, a terminal switching unit 32, a potential difference detection unit 33 that detects a potential difference between impedance measurement electrodes in the case where a constant current is applied thereto in order to detect an impedance, a slider control unit 34 including the stepping motor for controlling the sliding of the slide bar 402, and a sensor control unit 35 for controlling the laser sensor 403.

A control unit (including a CPU (central processing unit)) 10 in the computer 100 includes an electrode determination unit 11 and a computation processing unit 15.

Furthermore, a body build information measurement unit 24, an information input unit 25 for accepting various types of information such as body build information and attribute information of the measurement subject, a display unit 26, an operating unit 27, a power source unit 28, a memory unit 29, and multiple electrodes for measuring impedances are provided as well.

The electrode determination unit 11 includes an area detection unit 12 having the aforementioned predetermined area detection function and an electrode position setting 13 having the aforementioned electrode position setting function. The computation processing unit 15 includes an impedance measurement unit 16 and a fat mass calculation unit 17. The impedance measurement unit 16, meanwhile, includes an impedance calculation unit 161 that calculates an impedance in accordance with a predetermined computation formula and an electrode selection unit 162 that selects electrodes to be used in the impedance measurement. The fat mass calculation unit 17 includes an abdominal area fat mass calculation unit 18.

Upon being inputted with the light-received signal from the laser sensor 403 via the sensor control unit 35, the area detection unit 12 detects the rotational amount of the stepping motor in the slider control unit 34, and detects the position of the slide bar 402 along the slide rail 400 based on the detected rotational amount. Based on the detected position, the predetermined area of the trunk area (that is, the abdominal area) of the measurement subject who is lying face-up on the electrode mat 200 is detected.

The electrode position setting unit 13 sets the electrode pairs to be used in the impedance measurement. Specifically, a coordinate table 291 that holds coordinates (x, y) that correspond to the respective electrode pairs on the electrode mat 200 and indicate positions of those electrode pairs on the electrode mat 200 is stored in the memory unit 29. The electrode position setting unit 13 searches the coordinate table 291 based on the position of the detected predetermined area that corresponds to the long side of the electrode mat 200 (an X coordinate), and reads out the coordinates (x, y) corresponding to that position. Through this, the multiple electrode pairs that can make contact with the surface of the body at the predetermined area of the measurement subject who is lying face-up, or in other words, the coordinates (x, y) of the multiple electrode groups, can be detected. The coordinates (x, y) of the respective detected electrode pairs are outputted to the electrode selection unit 162 as electrode identification information.

In order to simplify the descriptions, the four electrode pairs in the multiple electrode groups that can make contact with the abdominal area rear surface are referred to as electrode pairs AP(1), AP(2), AP(3) and AP(4), corresponding to the respective rows AP1 to AP4 (see FIG. 3A). In FIG. 3A, the electrode group that makes contact with the measurement subject's abdominal area rear surface (the electrode pairs AP(1) to AP(4)), and upper limb electrodes H11 and H21 and lower limb electrodes F11 and F21 that are affixed to, for example, the measurement subject's upper and lower limbs, which serve as the areas distanced from the abdominal area, are shown as the impedance measurement electrodes.

The CPU in the control unit 10 controls the fat mass measurement apparatus 1 as a whole. Specifically, the control unit 10 sends instructions to the aforementioned functional blocks, performs various types of computation processes based on obtained information, and so on. The computation processing unit 15 processes these various types of computations.

The electrode pairs AP(1) to AP(4) in the respective electrode groups are affixed to the body surface at the measurement subject's abdominal area rear surface along the body axis direction. According to one or more embodiments of the present invention, the upper limb electrodes H11 and H21 are affixed to the body surface at the right wrist and the body surface at the left wrist. According to one or more embodiments of the present invention, the lower limb electrodes F11 and F21 are affixed to the body surface at the right ankle and the body surface at the left ankle. The electrode pairs of the electrode mat 200, the upper limb electrodes H11 and H21, and the lower limb electrodes F11 and F21 are electrically connected to the terminal switching unit 32. To simplify the descriptions, FIG. 3A shows a state in which the electrode pairs AP(1) to AP(4) of the electrode mat 200 are electrically connected to the terminal switching unit 32.

The terminal switching unit 32 includes, for example, a multiplexer circuit. The multiplexer circuit has multiple terminals. The electrode pairs of the electrode mat 200, as well as the upper limb electrodes H11 and H21 and the lower limb electrodes F11 and F21, are connected to respective terminals. The terminal switching unit 32 analyzes instructions from the electrode selection unit 162, and based on the results of the analyses, selects the terminals specified in the instructions from among the multiple terminals. Then, the multiplexer circuit is controlled so as to electrically connect the electrodes connected to the selected terminals with the constant current generation unit 31, and electrically connect the electrode pairs connected to the selected terminals with the potential difference detection unit 33.

Here, a correspondence relationship table 292 that holds a correspondence relationship between the electrode identification information of the electrodes (or electrode pairs) and terminal identification information of the terminals to which those electrodes (or electrode pairs) are connected is stored in the memory unit 29. Note that the electrode pair identification information is indicated by coordinates (x, y) of the electrode mat 200. The electrode selection unit 162 searches the correspondence relationship table 292 based on coordinates (x, y) of the electrode pairs provided by the electrode position setting unit 13, and reads out the terminal identification information of the terminals to which those electrode pairs are to be connected. A terminal switching instruction signal containing the read-out terminal identification information is generated and supplied to the terminal switching unit 32. As described above, the terminal switching unit 32 controls the multiplexer circuit based on the instruction signal from the electrode selection unit 162 so that the terminals specified by the terminal identification information contained in that instruction signal are connected to the constant current generation unit 31 or the potential difference detection unit 33.

As a result, the electrode pairs electrically connected to the constant current generation unit 31 by the terminal switching unit 32 function as constant current application electrode pairs, and the electrode pairs electrically connected to the potential difference detection unit 33 by the terminal switching unit 32 function as potential difference detection electrode pairs. The electrical connections made by the terminal switching unit 32 are switched at various times during measurement operations.

The constant current generation unit 31 generates a constant current based on an instruction received from the control unit 10, and supplies the generated constant current to the terminal switching unit 32. The constant current generation unit 31 supplies a high-frequency current (for example, 50 kHz, 500 µA) that can be used effectively for measuring body composition information. Through this, the constant current can be applied to the measurement subject via the electrode pairs electrically connected to the constant current generation unit 31 by the terminal switching unit 32, or in other words, via the constant current application electrode pairs.

The potential difference detection unit 33 detects a potential difference between the electrode pairs electrically connected to the potential difference detection unit 33 by the terminal switching unit 32, or in other words, between the electrodes in the potential difference detection electrode pairs, and outputs the detected potential difference to the control unit 10. Through this, the potential differences between the electrodes in the potential difference detection electrode pairs are detected in a state in which the aforementioned constant current is applied to the measurement subject.

The body build information measurement unit 24 and the information input unit 25 are elements for obtaining measurement subject information used in computation processes carried out by the computation processing unit 15 of the control unit 10. Here, "measurement subject information" refers to information regarding the measurement subject, and includes at least one of, for example, age, sex, body build information, and so on.

The body build information is information regarding the body size of the measurement subject, and includes, for example, information of a waist length (abdominal area circumferential length), abdominal area width and depth, abdominal area thickness, and the like, as well as information such as the height and weight. The body build information measurement unit 24 is an element that automatically measures the measurement subject's body build information, and outputs the measured body build information to the control unit 10. Meanwhile, the information input unit 25 is an element for inputting the measurement subject information, and outputs the inputted measurement subject information to the control unit 10.

Although the function block diagram shown in FIGS. 3A and 3B illustrates an example in which both the body build information measurement unit 24 and the information input unit 25 are provided in the fat mass measurement apparatus 1, it should be noted that the body build information measurement unit 24 and the information input unit 25 are not constituent elements that are absolutely necessary. Whether or not to provide the body build information measurement unit 24 and/or the information input unit 25 is selected as appropriate based on the types of measurement subject information used in the computation processes carried out by the computation processing unit 15 of the control unit 10. Furthermore, the configuration may be such that of the measurement subject information, the body build information is automatically measured by the body build information measurement unit 24, or is inputted by the measurement subject him/herself or an operator using the information input unit 25.

The impedance calculation unit 161 of the impedance measurement unit 16 calculates various types of impedances (called "body impedances") based on a current value of the constant current generated by the constant current generation unit 31 and potential difference information detected by the potential difference detection unit 33 and received by the control unit 10.

The fat mass calculation unit 17 calculates a fat mass based on impedance information obtained by the impedance calculation unit 161 and the measurement subject information received from the body build information measurement unit 24 and/or the information input unit 25. The fat mass calculation unit 17 includes the abdominal area fat mass calculation unit 18 that calculates the fat mass of the measurement subject's abdominal area. The fat mass calculated here refers to an index that indicates the mass of fat, and indicates a fat volume in the present embodiment.

The display unit 26 displays information of the fat mass calculated by the computation processing unit 15. An LCD (liquid-crystal display), for example, can be used as the display unit 26.

The operating unit 27 is an element for an operator to input commands to the fat mass measurement apparatus 1, and is configured of pushable keys, switches, and so on.

The power source unit 28 is an element for supplying electrical power to the control unit 10 and the like, and includes an internal power source such as a battery, an external power source such as an AC outlet, or the like.

The memory unit 29 includes a non-volatile memory. The memory unit 29 is an element for storing various types of data and programs related to the fat mass measurement apparatus 1, and stores, for example, the aforementioned measurement subject information, calculated fat masses, and programs for executing a fat mass measurement process, which will be described later.

Example of Electrode Arrangement Relative to Body

Figure 4:
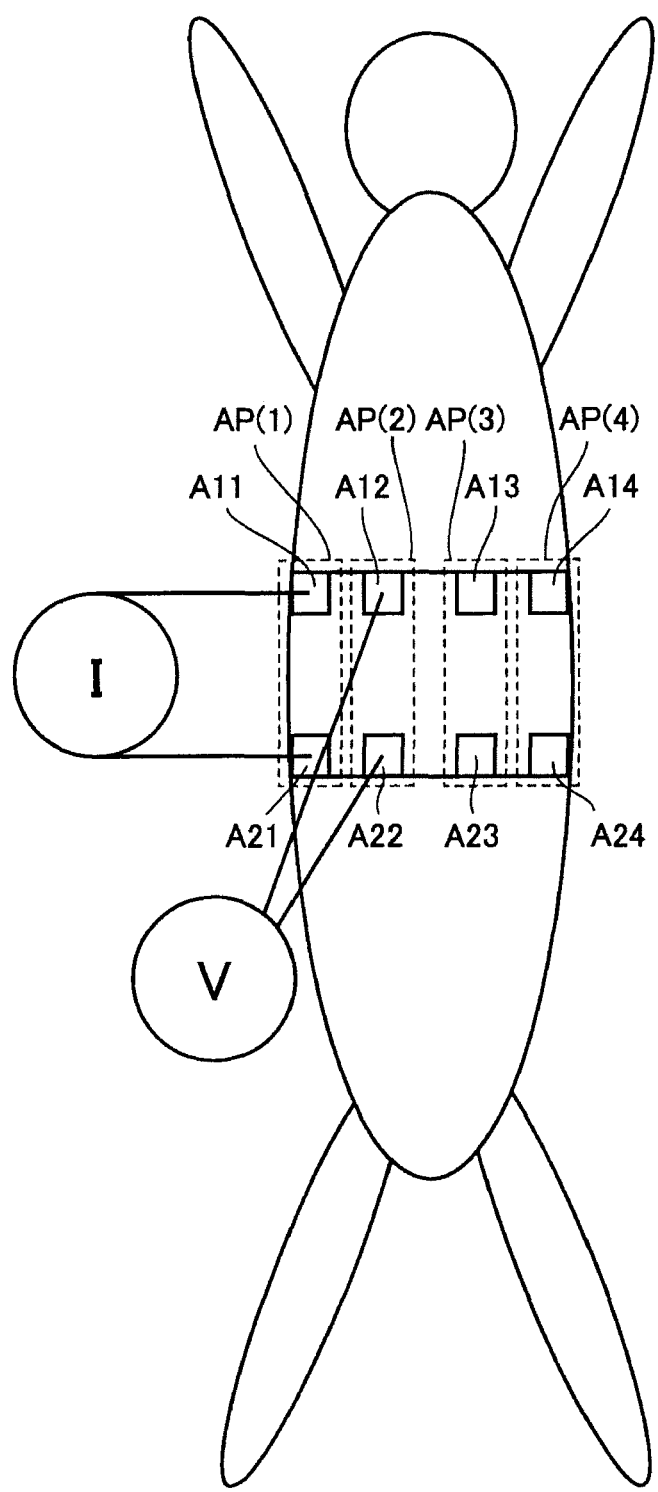
FIG. 4 is a diagram illustrating an example of the arrangement of electrodes according to the first embodiment of the present invention.

FIG. 4 illustrates an example of an electrode arrangement on the abdominal area when taking a measurement using the fat mass measurement apparatus 1 according to the first embodiment. FIG. 4 illustrates a state in which a single electrode group (a group composed of the four electrode pairs AP(1), AP(2), AP(3), and AP(4)) are arranged on the abdominal area, and the electrodes on the other areas are not shown.

As shown in FIG. 4, the electrode pair AP(1) includes electrodes A11 and A21. The electrode pair AP(2) includes electrodes A12 and A22. The electrode pair AP(3) includes electrodes A13 and A23. The electrode pair AP(4) includes electrodes A14 and A24.

When the measurement subject is lying face-up as shown in FIG. 1 and his/her abdominal area rear surface is in contact with the electrode mat 200, the electrode pairs AP(1), AP(2), AP(3), and AP(4) are disposed along the body axis direction on the measurement subject's abdominal area rear surface, and are disposed at intervals along the direction approximately perpendicular to the body axis. For example, the electrode pair AP(2) is disposed at a predetermined distance from an axis that passes through the electrodes A11 and A21 of the electrode pair AP(1).

The distances between the electrodes in the respective electrode pairs AP(1), AP(2), AP(3), and AP(4) are approximately equal. For example, the distance between the electrodes A11 and A21 of the electrode pair AP(1) is approximately equal to the distance between the abdominal area electrodes A12 and A22 of the electrode pair AP(2). The electrodes in each of the electrode pairs AP(1), AP(2), AP(3), and AP(4) are aligned with the electrodes in the corresponding other electrode pairs and along the direction approximately orthogonal to the body axis. In other words, the electrodes A11, A12, A13, and A14 are arranged in a single row in the direction approximately orthogonal to the body axis. The electrodes A21, A22, A23, and A24 are also arranged in a single row in the direction approximately orthogonal to the body axis.

The constant current generation unit 31 applies a current between the electrodes in the electrode pairs electrically connected to the constant current generation unit 31 by the terminal switching unit 32 (these will be called "current electrode pairs" hereinafter).

The potential difference detection unit 33 detects a potential difference between the electrodes in the electrode pairs electrically connected to the potential difference detection unit 33 by the terminal switching unit 32 (these will be called "voltage electrode pairs" hereinafter).

Fat Mass Calculation Procedure

Next, an example of a computation process carried out when calculating an abdominal area fat area and an abdominal area fat volume, which serve as indexes indicating fat mass, will be described.

Here, as shown in FIG. 4, it is assumed that one of the multiple electrode groups that can make contact with the abdominal area rear surface is selected. The impedance calculation unit 161 calculates two types of impedances based on the value of the current generated by the constant current generation unit 31 and the potential difference detected by the potential difference detection unit 33. One of the two types of impedances is an impedance reflecting a non-fat mass in the measurement subject's abdominal area (this impedance will be labeled "Zt" hereinafter). The other impedance is an impedance reflecting a subcutaneous fat mass in the measurement subject's abdominal area (this impedance will be labeled "Zs" hereinafter).

The abdominal area fat mass calculation unit 18 calculates the measurement subject's abdominal area fat area (unit: $cm^2$) based on the two types of calculated impedances Zt and Zs and the body build information (waist length) of the measurement subject. Specifically, an abdominal area fat area Sv is calculated through, for example, the following Formula (1), which expresses a relationship between the two types of impedances Zt and Zs and waist length of the measurement subject and the abdominal area fat area.

$$Sv = a \times W^2 - b \times (1/Zt) - c \times W \times Zs - d \quad (1)$$

(Here, a, b, c, and d are coefficients, and W represents the waist length.)

As described above, when the abdominal area fat area Sv has been calculated using one of the electrode groups, the electrode selection unit 162 selects the electrode group for the next area from among the multiple electrode groups that can make contact with the abdominal area rear surface. The electrode selection unit 162 outputs, to the terminal switching unit 32, an electrification instruction that contains identification information of each electrode pair in the selected electrode groups for the next area.

As a result, the constant current is applied, the potential difference is detected, the impedance calculation unit 161 calculates the impedances Zt and Zs, and the abdominal area fat mass calculation unit 18 calculates the abdominal area fat area Sv for the electrode group for the next area (the group consisting of the electrode pairs AP(1), AP(2), AP(3), and AP(4)), in the same manner as described above.

Thereafter, the multiple electrode groups that can make contact with the abdominal area rear surface are selected in order, and the abdominal area fat area Sv is calculated using the selected electrode groups.

Figure 5:
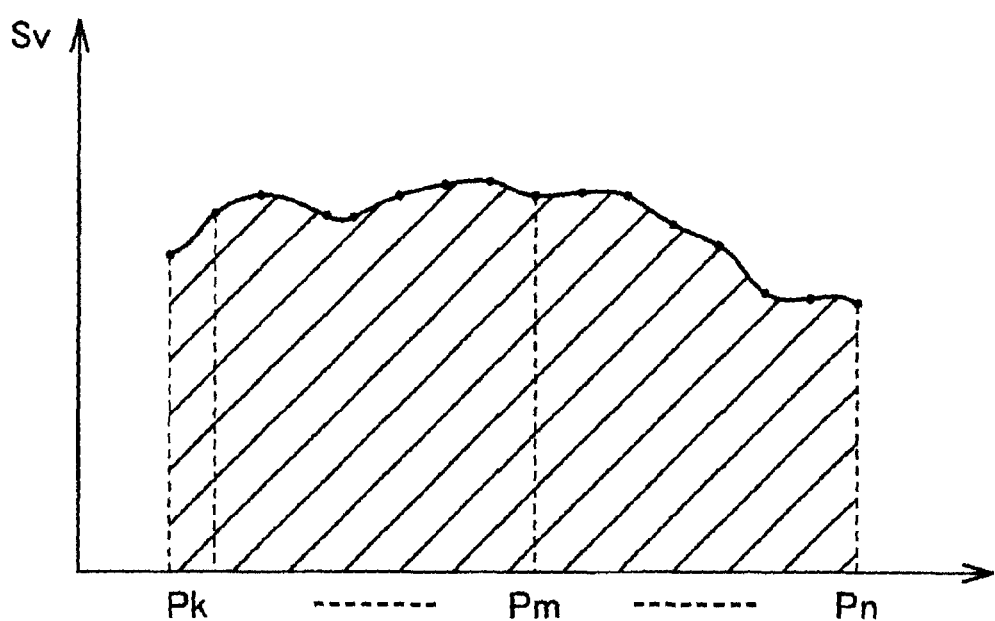
FIG. 5 is a diagram illustrating a procedure for calculating a fat volume in an abdominal area according to the first embodiment of the present invention.

A principle of the procedure for calculating the abdominal area fat volume as carried out by the abdominal area fat mass calculation unit 18 will be described with reference to FIG. 5. As described earlier, the electrode position setting unit 13 sets the positions, on the electrode mat 200, of the multiple electrode groups to be used in the fat mass measurement, based on the position of the predetermined area detected by the area detection unit 12. It is assumed that the predetermined position is a position Pi (where i=1, 2, 3, . . . k, . . . n) in FIG. 5. During operations, the electrode groups at each position Pi are selected by the electrode selection unit 162, and the abdominal area fat area Sv indicated by the vertical axis in FIG. 5 is calculated using the selected electrode groups. Then, by integrating the abdominal area fat areas Sv calculated at each position Pi, a abdominal area fat volume, indicated by the diagonally-hatched lines in FIG. 5, is calculated.

Measurement Process

An example of the measurement process according to the first embodiment will be described based on the flowcharts illustrated in FIG. 6 and FIG. 7.

Figure 6:
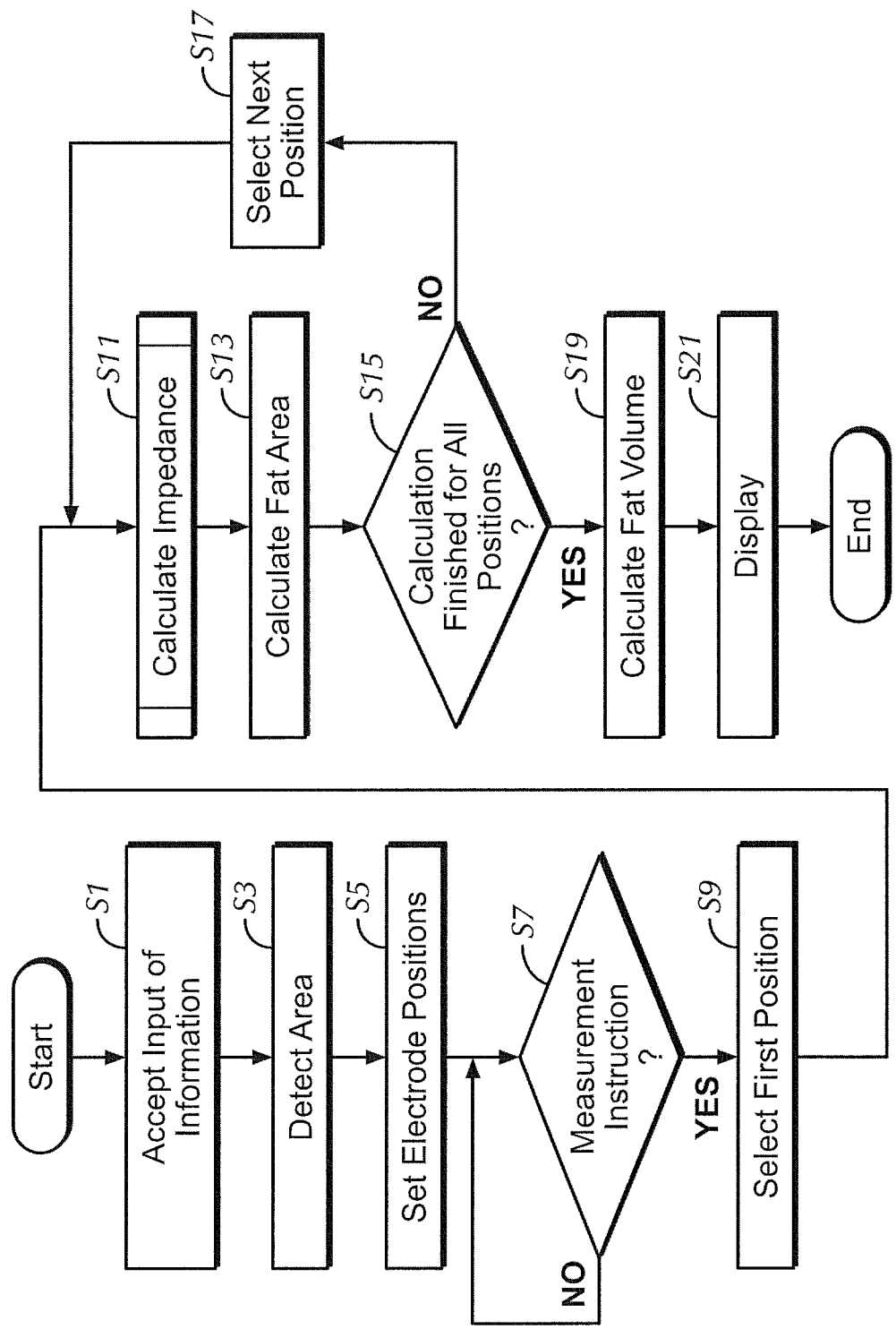
FIG. 6 is a flowchart illustrating a measurement process according to the first embodiment of the present invention.
Figure 7:
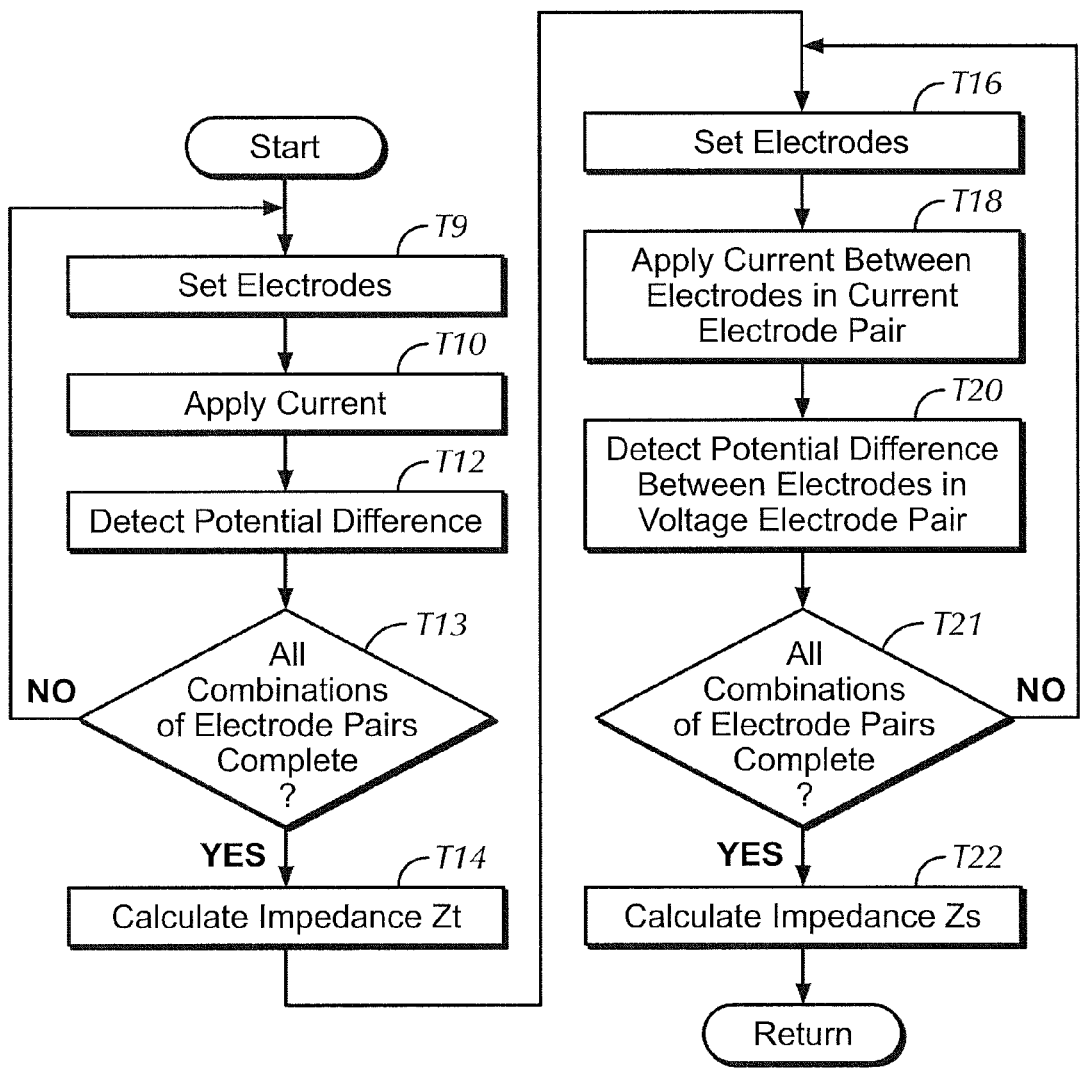
FIG. 7 is a flowchart illustrating the measurement process according to the first embodiment of the present invention.

The flowcharts in FIG. 6 and FIG. 7 are held in the memory unit 29 in advance as programs. The processes are realized by the CPU of the control unit 10 reading out the programs from the memory unit 29 and executing the respective commands in the programs.

As shown in FIG. 6, first, the CPU of the control unit 10 inputs various types of information via the operating unit 27, the body build information measurement unit 24, and the information input unit 25 (step S1).

Next, an instruction signal is outputted to the slider control unit 34 so that the slider 401 slides along the slide rail 400, and an instruction signal is outputted to the sensor control unit 35 so that the laser sensor 403 emits/receives laser light. The slider control unit 34 causes the slider 401 to slide along the slide rail 400 in accordance with the instruction signal, and at the same time, the sensor control unit 35 causes the laser sensor 403 to emit laser light in accordance with the instruction signal. When the laser sensor 403 has reached the positions corresponding to the marks 201 and 202 as a result of the sliding, the laser light reflected by the marks 201 and 202 is received by the laser sensor 403, and the light-received signals are outputted. The area detection unit 12 detects the position, on the electrode mat 200, of the predetermined area of the trunk area (that is, the abdominal area) based on the position of the slide bar 402 along the slide rail 400 when the light-received signal is inputted (this is detected from the rotational amount of the stepping motor) (step S3).

Next, the electrode position setting unit 13 determines the positions (the coordinates (x, y)), on the electrode mat 200, of the electrode pairs in the multiple electrode groups to be used in the fat mass measurement, based on the detected position of the predetermined area (step S5). Here, it is assumed that the determined position corresponds to the position Pi (where i=k, ... m, ... n) in FIG. 5. The electrode position setting unit 13 outputs the positions determined for the electrode pairs in each electrode group to the electrode selection unit 162 as the electrode identification information.

Next, it is determined whether or not a measurement instruction has been inputted by the operator via the operating unit 27 (step S7). The CPU stands by for the input of a measurement instruction during the period when it is determined that there is no measurement instruction (NO in step S7).

When it has been determined that a measurement instruction has been made (YES in step S7), the electrode selection unit 162 selects the position Pi of the first electrode group to be used in the impedance measurement (that is, i=k), and the instruction signal including the terminal identification information corresponding to the electrode pairs in the selected electrode group is outputted to the terminal switching unit 32 (step S9).

Then, the terminal switching unit 32 controls the multiplexer circuit so that the terminals indicated by the terminal identification information in the supplied instruction signal are electrically connected to the constant current generation unit 31 or the potential difference detection unit 33. Through this, the impedance calculation unit 161 calculates the impedance in accordance with the aforementioned Formula (1), using the electrode pairs in the electrode group electrically connected to the constant current generation unit 31 or the potential difference detection unit 33 (step S11). The process for calculating this impedance will be mentioned later.

Next, the abdominal area fat mass calculation unit 18 calculates the abdominal area fat area Sv based on the impedance calculated in step S11 (step S13).

After the abdominal area fat area Sv has been calculated, in step S15, the CPU determines whether or not the calculation of the abdominal area fat areas Sv using the multiple electrode groups determined by the electrode position setting unit 13 in step S5 has ended (step S15). In other words, it is determined whether or not the impedance calculation carried out using the electrode group at the position Pn shown in FIG. 5 has ended.

If it is determined that the calculation has ended (YES in step S15), the processing advances to step S19, which will be mentioned later; however, if it is determined that the calculation has not ended (NO in step S15), the electrode selection unit 162 selects the electrode group at the next position, or the position Pi (where i=i+1) (step S17). After this, the impedance is measured using the selected electrode group at the next position (step S11).

In this manner, the processes from steps S11 to S17 are repeated for each electrode group that can make contact with the predetermined area (the abdominal area rear surface) detected by the area detection unit 12, or in other words, for each of the electrode groups at positions Pk through Pn. As a result, the abdominal area fat area Sv is calculated using the impedances measured using the respective electrode groups (that is, the respective electrode groups corresponding to the positions Pk through Pn in FIG. 5).

In step S19, the abdominal area fat mass calculation unit 18 calculates the abdominal area fat volume by integrating the abdominal area fat areas Sv. The calculated fat volume is then displayed via the display unit 26 (step S21).

FIG. 7 illustrates a flowchart of the impedance measurement process (step S11).

First, a process for calculating the impedance Zt is carried out.

Based on the supplied instruction signal, the terminal switching unit 32 selects, for example, a pair consisting of the upper limb electrode H11 and the lower limb electrode F11 and a pair consisting of the upper limb electrode H21 and the lower limb electrode F21 as respective current electrode pairs, and sets the electrode pair AP(1) specified by the terminal identification information as a voltage electrode pair. In other words, through the multiplexer circuit, the terminal switching unit 32 electrically connects the pair consisting of the upper limb electrode H11 and lower limb electrode F11 and the pair consisting of the upper limb electrode H21 and lower limb electrode F21 to the constant current generation unit 31, and electrically connects the electrode pair AP(1) to the potential difference detection unit 33 (step T9). Here, based on the instruction signal from the electrode selection unit 162, the terminal switching unit 32 cuts the electrical connection between unselected electrodes and the constant current generation unit 31 and potential difference detection unit 33.

The constant current generation unit 31 applies a current in the direction from the upper limbs toward the lower limbs based on the instruction signal from the CPU of the control unit 10. For example, the constant current generation unit 31 applies a current from the upper limb electrode H11 and upper limb electrode H21 toward the lower limb electrode F11 and lower limb electrode F21 (step T10). In this case, according to one or more embodiments of a configuration in which the terminal switching unit 32 shorts between the upper limb electrode H11 and upper limb electrode H21 and shorts between the lower limb electrode F11 and lower limb electrode F21 is employed. Note that the constant current generation unit 31 and the terminal switching unit 32 may be configured to apply a current from one of the upper limb electrodes H11 and H21 to one of the lower limb electrodes F11 and F21.

In this state, the potential difference detection unit 33 detects a potential difference between the electrodes A11 and A21 of the electrode pair AP(1) based on an instruction signal from the CPU of the control unit 10 (step T12).

The terminal switching unit 32 then sets the electrode pairs AP(2), AP(3), and AP(4) of the selected electrode group as the voltage electrode pairs, in that order. In other words, the terminal switching unit 32 electrically connects the electrode pairs AP(2), AP(3), and AP(4) in order to the potential difference detection unit 33, based on an instruction signal from the CPU of the control unit 10 (step T9). Then, the potential difference detection unit 33 sequentially detects a potential difference between the electrodes in the electrode pairs AP(2), AP(3), and AP(4) based on an instruction signal from the CPU of the control unit 10 (step T12).

In the case where the detection of potential differences has been completed for all of the electrode pair combinations, which here is a case in which potential differences have been detected between the electrodes in the electrode pairs AP(1), AP(2), AP(3), and AP(4) (YES in step T13), the impedance calculation unit 161 calculates impedances Zt1 through Zt4 based on the value of the current applied by the constant current generation unit 31 and the potential differences detected by the potential difference detection unit 33 (step T14). The values of the impedances Zt1 through Zt4 calculated by the impedance calculation unit 161 are temporarily stored in, for example, the memory unit 29.

Next, the impedance Zs is calculated.

That is, the terminal switching unit 32 sets the electrode pair AP(1) as the current electrode pair, and sets the electrode pair AP(2) as the voltage electrode pair. In other words, the terminal switching unit 32 electrically connects the electrode pair AP(1) to the constant current generation unit 31, and electrically connects the electrode pair AP(2) to the potential difference detection unit 33 (step T16). Here, based on an instruction signal from the CPU of the control unit 10, the terminal switching unit 32 electrically connects the electrode pairs in the selected electrode group to the potential difference detection unit 33 in a selective manner, and cuts the electrical connection between the unselected electrode pairs, upper limb electrodes, and lower limb electrodes and the constant current generation unit 31 and potential difference detection unit 33.

The constant current generation unit 31 applies a current between the electrodes A11 and A21 of the electrode pair AP(1) based on the instruction signal from the CPU of the control unit 10 (step T18).

In this state, the potential difference detection unit 33 detects a potential difference between the electrodes A12 and A22 of the electrode pair AP(2) based on an instruction signal from the CPU of the control unit 10 (step T20).

The terminal switching unit 32 then sets the electrode pairs AP(3) and AP(4) as the voltage electrode pairs, in that order. In other words, the terminal switching unit 32 electrically connects the electrode pairs AP(3) and AP(4), in order, to the potential difference detection unit 33 (step T16). Then, the potential difference detection unit 33 sequentially detects a potential difference between the electrodes in the electrode pairs AP(3) and AP(4) based on an instruction signal from the CPU of the control unit 10 (step T20).

Next, the terminal switching unit 32 sets the electrode pair AP(2) as the current electrode pair, and sets the electrode pair AP(1) as the voltage electrode pair. In other words, the terminal switching unit 32 electrically connects the electrode pair AP(2) to the constant current generation unit 31, and electrically connects the electrode pair AP(1) to the potential difference detection unit 33 (step T16).

The constant current generation unit 31 applies a current between the electrodes A12 and A22 of the electrode pair AP(2) based on the instruction signal from the CPU of the control unit 10 (step T18).

In this state, the potential difference detection unit 33 detects a potential difference between the electrodes A11 and A21 of the electrode pair AP(1) based on an instruction signal from the CPU of the control unit 10 (step T20).

The terminal switching unit 32 then sets the electrode pairs AP(3) and AP(4) as the voltage electrode pairs, in that order. In other words, the terminal switching unit 32 electrically connects the electrode pairs AP(3) and AP(4), in order, to the potential difference detection unit 33 (step T16). Then, the potential difference detection unit 33 sequentially detects a potential difference between the electrodes in the electrode pairs AP(3) and AP(4) based on an instruction signal from the CPU of the control unit 10 (step T20).

In the same manner, the terminal switching unit 32 carries out control that sets the electrode pairs AP(3) and AP(4) as the current electrode pairs in order, sets the electrode pairs AP(1) to AP(4) that are not current electrode pairs as the voltage electrode pairs in order for each of the electrode pairs AP(3) and AP(4), and detects the potential differences between the electrodes in the voltage electrode pairs (steps T16 through T20).

For the electrode group selected in step S9 (or S17), in the case where the current application and potential difference detection has been completed for all combinations of the electrode pairs (electrode pairs AP(1) to AP(4)) in that electrode group (YES in step T21), the impedance calculation unit 161 calculates impedances Zs1 to Zs12 based on the value of the current applied by the constant current generation unit 31 and the potential differences detected by the potential difference detection unit 33 (step T22). The values of the impedances Zs1 to Zs12 calculated by the impedance calculation unit 161 are temporarily stored in, for example, the memory unit 29.

This ends the impedance calculation process of step S11.

Returning to FIG. 6, in step S13, the abdominal area fat mass calculation unit 18 calculates the abdominal area fat areas Sv based on the body build information (waist length) received in step S1 and the impedances Zt1 through Zt4 and impedances Zs1 to Zs12 calculated in step S11. The abdominal area fat areas Sv are calculated through the aforementioned Formula (1).

Note that in the case where the electrode group includes the four electrode pairs AP(1) to AP(4), for example, the average value of the four impedances Zt1 through Zt4 is substituted for the impedance Zt in Formula (1), and the average value of the twelve impedances Zs1 to Zs12 is substituted for the impedance Zs in Formula (1).

The abdominal area fat volume can be calculated through the measurement carried out according to the flowcharts shown in FIG. 6 and FIG. 7.

The fat mass measurement apparatus 1 according to the first embodiment measures the impedances using the electrode pairs AP(1) to AP(4) that are arranged along the measurement subject's abdominal area rear surface in the direction of the body axis. Accordingly, differences in curvature angles between electrodes in the current electrode pair and differences in curvature angles between electrodes in the voltage electrode pair can be reduced among measurement subjects having different abdominal area shapes, or in other words, different extents to which the abdominal area protrudes in the direction parallel to the abdominal area side cross-section. Through this, variations in the detection range and detection sensitivity of the potential differences among measurement subjects caused by differences in the curvature degrees between electrodes can be reduced. In addition, fluctuations in the potential differences caused by fluctuations in the positions of the electrodes in the direction parallel to the abdominal area side cross-section arising due to breathing can also be reduced. Accordingly, the fat mass measurement apparatus 1 according to the first embodiment makes it possible to improve the measurement accuracy.

In addition, the multiple impedances Zt and multiple impedances Zs are calculated based on the potential differences between electrodes in each electrode pair measured using the multiple electrode pairs AP(1), AP(2), AP(3), and AP(4), and the fat volume is calculated using the average values of the impedances Zt and the impedances Zs. Through this, it is possible to eliminate the influence of variations in fat distributions and fat thicknesses.

Although the impedance calculation unit 161 is described in the flowchart of FIG. 7 as calculating the impedances all at once after the potential differences corresponding to all combinations of electrode pairs have been detected, it should be noted that embodiments of the invention are not limited thereto. The configuration may be such that an impedance is calculated each time a potential difference is detected between electrodes in an electrode pair. In addition, the selection order for the current electrode pairs and the voltage electrode pairs is not limited to the order illustrated in the flowchart of FIG. 7. Furthermore, the configuration may be such that the impedances Zt are calculated after calculating the impedances Zs.

In addition, although a configuration in which the abdominal area fat mass calculation unit 18 substitutes the average value of the impedances Zt1 through Zt4 for the impedance Zt in Formula (1) and substitutes the average value of the impedances Zs1 to Zs12 for the impedance Zs in Formula (1) is described in the flowchart of FIG. 7, embodiments of the invention are not limited thereto. The impedance calculation unit 161 calculates the impedance Zt based on an average value of the multiple potential differences detected in the case where a current is applied between the upper limb electrodes and the lower limb electrodes. In addition, the configuration may be such that the impedance calculation unit 161 calculates the impedance Zs based on an average value of the multiple potential differences detected in the case where a current is applied between the electrodes in an abdominal area electrode pair.

In addition, the configuration may be such that the impedance calculation unit 161 is provided with correlation functions for the impedances Zt and Zs, and calculates the impedances Zt and Zs. In addition, the configuration may be such that representative values are selected for the impedances Zt and Zs, respectively. The representative values are selected based on a predetermined condition, such as, for example, the maximum value or the like of the multiple impedances that have been calculated.

Furthermore, although the abdominal area fat area Sv is calculated using the waist length, which is the circumferential length of the trunk area, as the body build information in Formula (1), the invention is not limited thereto, and the abdominal area width and abdominal area thickness may be used as the body build information instead of the waist length.

Other Example of Position Detection Function

Although the first embodiment uses the laser sensor 403 in order to detect a predetermined position of the measurement subject's trunk area, the invention is not limited thereto. The marks 201 and 202 may be configured of magnets, and a magnetic sensor that detects the magnetic fields of those magnets may be used. Alternatively, an ultrasound sensor may be used. Ultrasound waves may be emitted from a sensor head, and the positions of the marks 201 and 202 may be detected when ultrasound waves reflected by the marks 201 and 202 have been received.

These techniques detect the predetermined position of the trunk area in a non-contact manner, but a contact-based technique may be used in the detection. For example, position detection using a pressure sensor, which is one example of a contact-based sensor, will be described.

As shown in FIG. 1, a mat 404 is installed in the bed. The mat 404 is placed across the entire surface of the bed on which the measurement subject lies face-up, and is approximately rectangular in shape. The direction in which the long side of the mat 404 extends matches the lengthwise direction of the bed.

The mat 404 includes multiple pressure sensors (not shown) arranged in a matrix. The pressure sensors measure pressure through diaphragms using pressure-sensitive elements, convert the measured pressures into electric signals, and output those electric signals.

Figure 8:
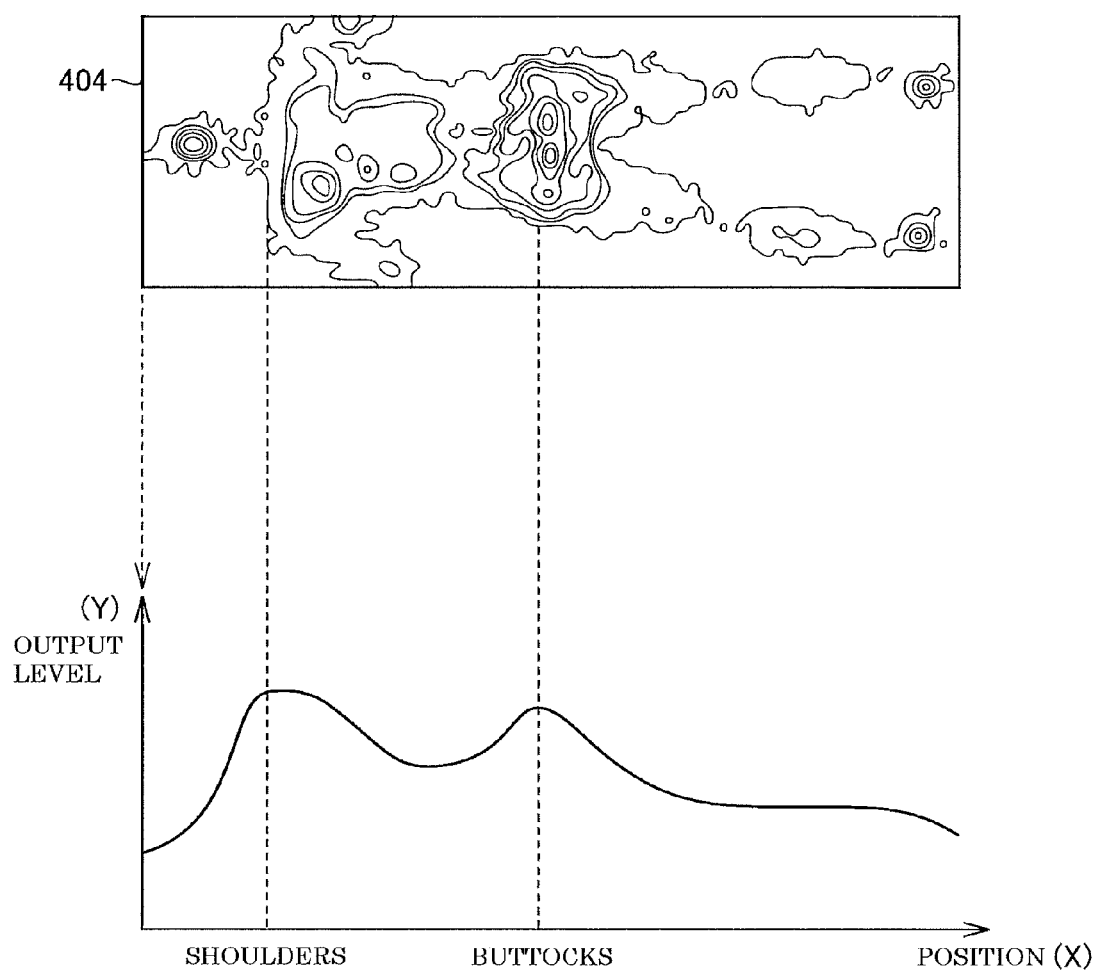
FIG. 8 is a diagram illustrating another method for detecting a predetermined location in a trunk area according to the first embodiment of the present invention.

When the measurement subject is lying face-up as shown in FIG. 1, pressure produced by the measurement subject's body weight is outputted as signals from the respective pressure sensors. The upper section of FIG. 8 illustrates a distribution of the output levels of the pressure sensors in the mat 404, or in other words, a distribution of the pressure is measured in this case. Meanwhile, assuming that in the graph shown in the lower section of FIG. 8, the vertical axis (Y axis) represents an output level of the pressure sensors and the horizontal axis (X axis) represents positions of the pressure sensors in the direction in which the long side of the mat 404 extends, the pressure distribution shown in the upper section of FIG. 8 can be converted into the graph shown in the lower section of FIG. 8.

If the measurement subject is face-up, the weight on the mat 404 is higher at the areas that correspond to the shoulders and the pelvis, as shown in the upper section of FIG. 8. Accordingly, a predetermined position in the measurement subject's trunk area (that is, the positions of the shoulders and pelvis) can be detected by calculating extreme points (that is, points with the largest changes) in the graph in the lower section of FIG. 8 through a differential process or the like. Here, because the long side of the mat 404 and the long side of the electrode mat 200 are parallel, detecting the predetermined position in the measurement subject's trunk area as a position along the long side of the mat 404 makes it possible to convert that predetermined position into a position along the long side of the electrode mat 200.

The area detection unit 12 can then detect the predetermined area of the trunk area on the electrode mat 200 based on the positions of the shoulders and pelvis along the long side of the electrode mat 200 and information of the measurement subject's height.

Although the mat 404 is described here as being provided separate from the electrode mat 200, it should be noted that the two mats may be configured integrally.

Second Embodiment

Although the aforementioned first embodiment describes measuring an impedance by bringing electrodes into contact with the rear surface of the measurement subject's abdominal area, the area where the electrodes make contact is not limited to the abdominal area rear surface, and as described in the present second embodiment, may be the abdominal area front surface instead.

An external view of a fat mass measurement apparatus 1A according to the second embodiment of the present invention will be described with reference to FIG. 9. The fat mass measurement apparatus 1A includes a computer 100A and a control unit 101A in place of the computer 100 and control unit 101 of the fat mass measurement apparatus 1.

In the present second embodiment, electrodes on an electrode support member 120 having a frame member 110 that can be attached so as to span the widthwise direction of the bed are used as the impedance measurement electrodes on the abdominal area of the measurement subject who is lying face-up on the bed, rather than the electrode mat 200.

Figure 9:
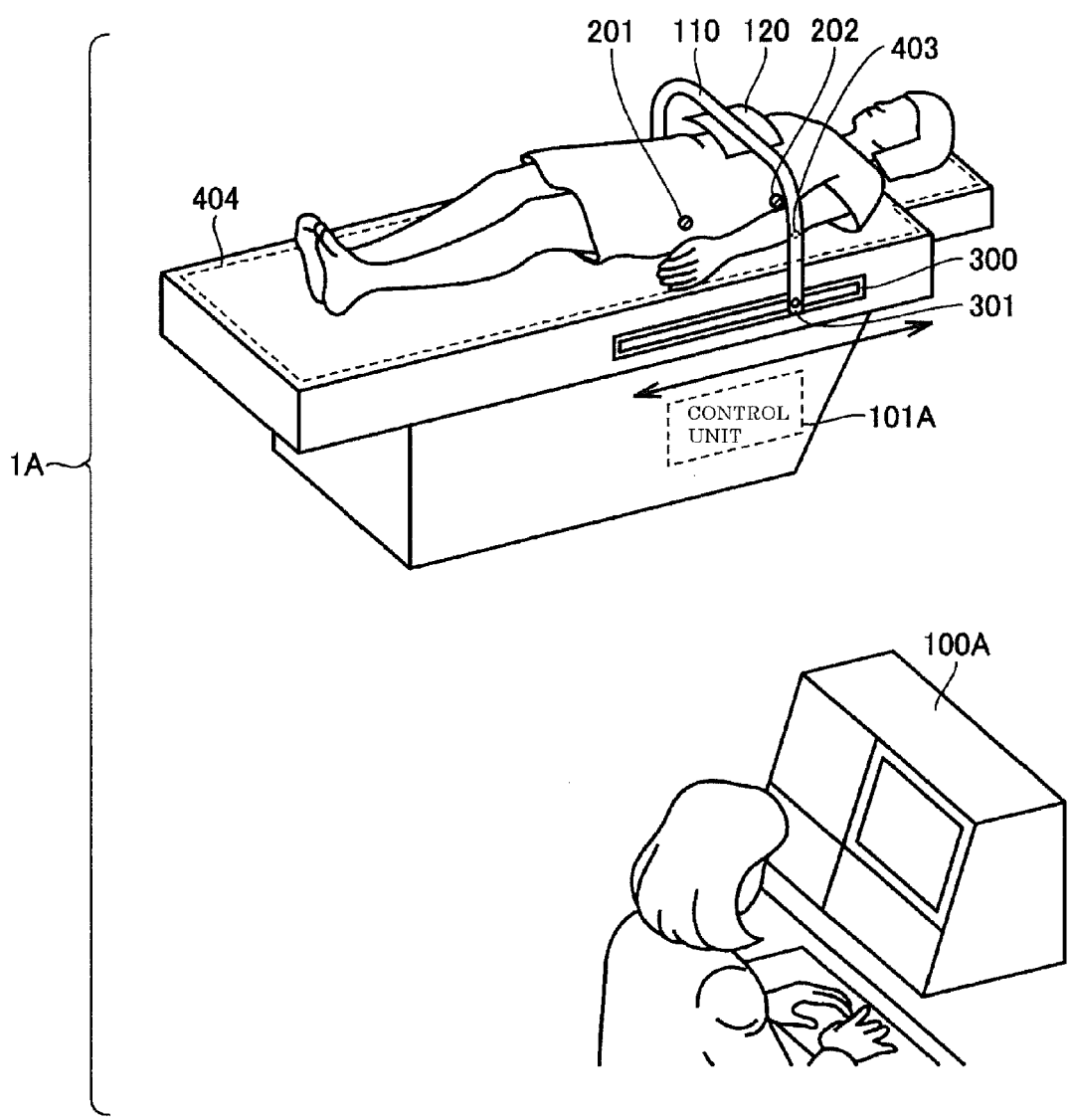
FIG. 9 is an external view of a fat mass measurement apparatus according to a second embodiment of the present invention.

Note that in FIG. 9, the measurement subject's clothing is designed so that the cloth on the abdominal area front surface side can be removed. Accordingly, during measurement, the electrodes provided in the electrode support member 120 can be brought into contact with the body surface on the abdominal area front surface side when the measurement subject is lying face-up, as shown in FIG. 9.

A slide rail 300 that extends along the lengthwise direction of the bed is formed on a side surface (the side surface visible in the front in FIG. 9) that extends in the lengthwise direction of the bed. A slider 301 is embedded in the slide rail 300. One end of the rod-shaped frame member 110 is connected to the slider 301 in a removable state. The frame member 110 is assumed to be affixed to the slider 301 when the measurement subject has laid face-up on the bed and measurement can be started. In the case where the frame member 110 is connected to the slider 301, the frame member 110 moves freely along the slide rail 300 with the slider 301, or in other words, along the lengthwise direction of the bed, when the slider 301 slides along the slide rail 300.

Note that another slide rail (not shown) that extends along the lengthwise direction of the bed is also formed on the other side surface that extends in the lengthwise direction of the bed, and the other end of the frame member 110 moves freely along this other slide rail in the same manner as the one end.

The slider 301 is connected to a rotating shaft of a stepping motor (not shown) in the control unit 101A, and slides in a direction and at a distance based on the rotation direction and rotation angle (also called "rotational amount" hereinafter) of the stepping motor. Accordingly, the position of the slider 301 along the slide rail 300, or in other words, the position of the electrodes in the electrode support member 120 integrally provided on the frame member 110, can be uniquely detected based on the rotational amount of the stepping motor.

Position Detection Function and Predetermined Area Detection Function

The laser sensor 403 is attached to the frame member 110. The laser sensor 403 is attached at a position at which the marks 201 and 202 affixed to the measurement subject who is lying face-up can be irradiated with laser light.

During operations, the laser sensor 403 emits laser light while the frame member 110, which is attached integrally to the slider 301, slides along the slide rail 300. When the slider 301 moves and reaches a position on the slide rail 300 that corresponds to the marks 201 and 202, the emitted laser light is reflected by the marks 201 and 202. The reflected light is received by a light-receiving portion of the laser sensor 403. The laser sensor 403 outputs a light-received signal when the light reflected by the marks 201 and 202 has been received. Accordingly, the positions of the slider 301 along the slide rail 300 when the light-received signal is detected corresponds to the positions of the marks 201 and 202.

Here, as in the first embodiment, the marks 201 and 202 are applied to the vicinity of the twelfth rib and the ilium, respectively, which serve as indicators for areas in the abdominal area, and thus a position on the slide rail 300 that corresponds to the abdominal area can be detected based on the positions of the marks 201 and 202 along the slide rail 300 detected using the light-received signal from the laser sensor 403 and information of the measurement subject's height.

Note that as in the first embodiment, in the present second embodiment as well, only one of the marks 201 and 202 may be affixed, the position of that mark may be detected based on the light-received signal from the laser sensor 403, and the position of the other mark may then be detected based on the detected position and the measurement subject's height.

In addition, the mat 404 is also disposed so that the long side thereof is parallel to the slide rail 300 in the present second embodiment as well. Then, as shown in FIG. 8, the positions of the shoulders and the pelvis may be detected based on the outputs of the respective pressure sensors, and the position on the slide rail 300 that corresponds to the abdominal area may then be detected based on the detected positions.

Figure 10:
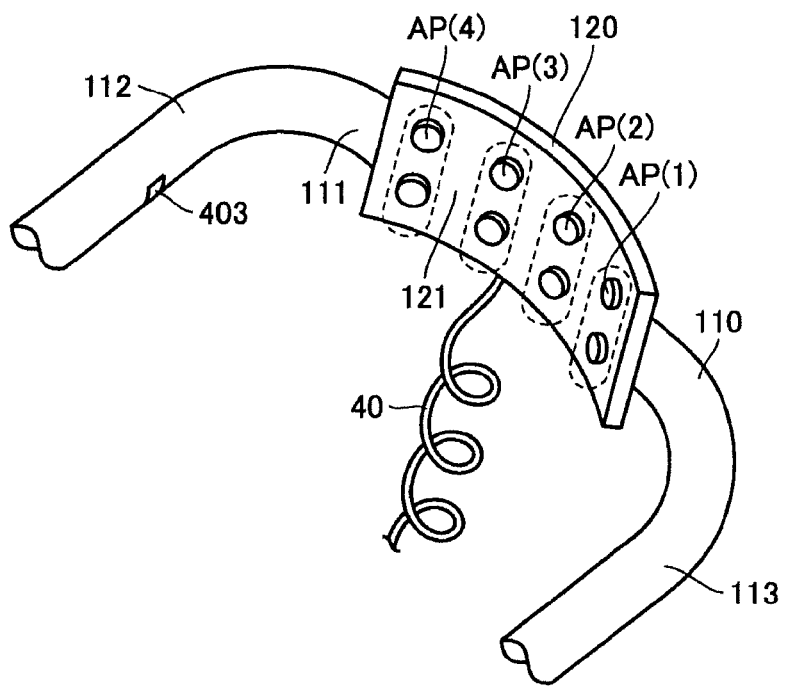
FIG. 10 is a diagram illustrating a frame member, an electrode support member, and a connection state between the two according to the second embodiment of the present invention.
Figure 11:
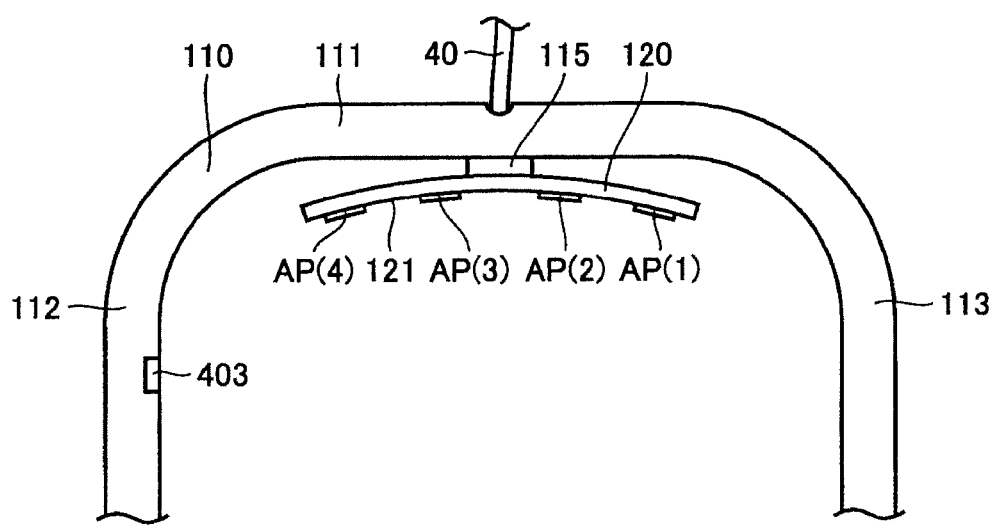
FIG. 11 is a diagram illustrating the frame member, the electrode support member, and the connection state between the two according to the second embodiment of the present invention.
Figure 12:
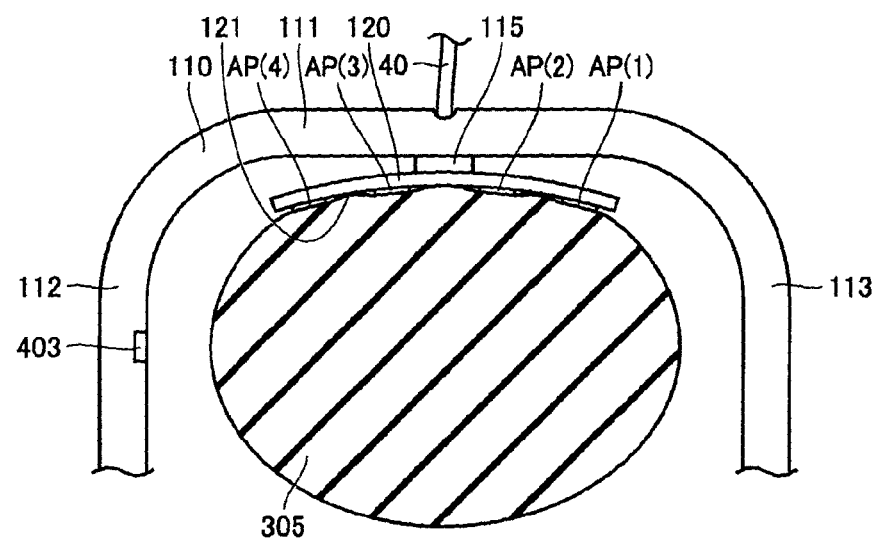
FIG. 12 is a diagram illustrating the frame member, the electrode support member, and the connection state between the two according to the second embodiment of the present invention.

The frame member 110 has a gate shape that can be attached to the bed so as to span the trunk area of the measurement subject who is lying face-up on the bed (see FIG. 9). FIGS. 10 through 12 illustrate connection states of the frame member 110, the electrode support member 120, and both of those members. As shown in these drawings, the frame member 110 includes a rod-shaped front frame portion 111, a rod-shaped left frame portion 112, a rod-shaped right frame portion 113, and the electrode support member 120 that is attached to the front frame portion 111. The laser sensor 403 is attached to the left frame portion 112 of the frame member 110 at a position at which the measurement subject who is lying face-up can be irradiated with laser light.

The electrode support member 120 is disposed in approximately the center of the front frame portion 111 of the frame member 110 so as to protrude inward. The electrode support member 120 is configured of a curved plate that is bent so that both ends thereof are positioned forward and the center thereof is positioned rearward. The aforementioned electrode pairs AP(1) to AP(4) are provided so as to be exposed on a front surface 121 of the electrode support member 120, and according to one or more embodiments of the present invention, the electrode pairs AP(1) to AP(4) protrude slightly from the front surface 121 of the electrode support member 120. The electrode support member 120 is positioned and attached on the front frame portion 111 so that the electrode pairs AP(1) to AP(4) face the abdominal area front surface of the measurement subject during measurement as shown in FIG. 9. A cable 40 for electrically connecting the electrode pairs AP(1) to AP(4) to the terminal switching unit 32 is connected to the electrode support member 120.

Meanwhile, as shown in FIG. 11, the electrode support member 120 is attached to the front frame portion 111 of the frame member 110 via a connection portion 115 including, for example, a ball joint. Through this, the electrode support member 120 is supported by the front frame portion 111 so as to be capable of swinging. Note that the electrode support member 120 is capable of swinging in a direction approximately orthogonal to the body axis. Accordingly, during measurement, the frame member 110 can be freely moved along the slide rail 300 while the electrode pairs AP(1) to AP(4) provided on the front surface 121 of the electrode support member 120 are brought into contact with the front surface of an abdominal area 305 of the measurement subject (see FIG. 12), at a steady and appropriate pressure.

Alternatively, the connection portion 115 may be provided with an elastic member such as a spring, and configured so that the electrode support member 120 is elastically supported on the front frame portion 111. Even if such an elastic member is used, the electrode pairs AP(1) to AP(4) can be brought into contact with the front surface of the abdominal area 305 of the measurement subject (see FIG. 12), at a steady and appropriate pressure.

Figure 13A:
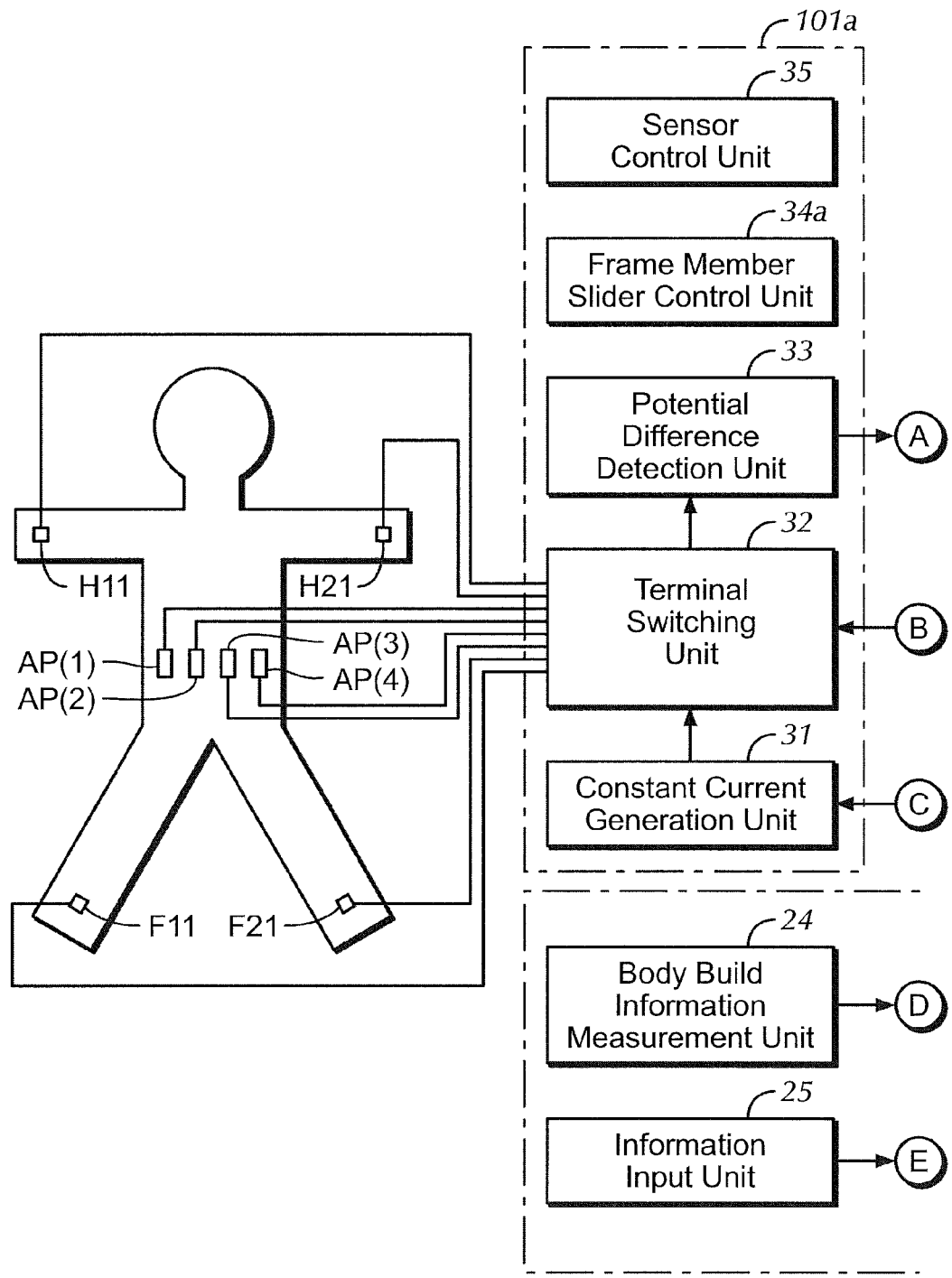
FIGS. 13A and 13B are diagrams illustrating a functional configuration of the fat mass measurement apparatus according to the second embodiment of the present invention.
Figure 13B:
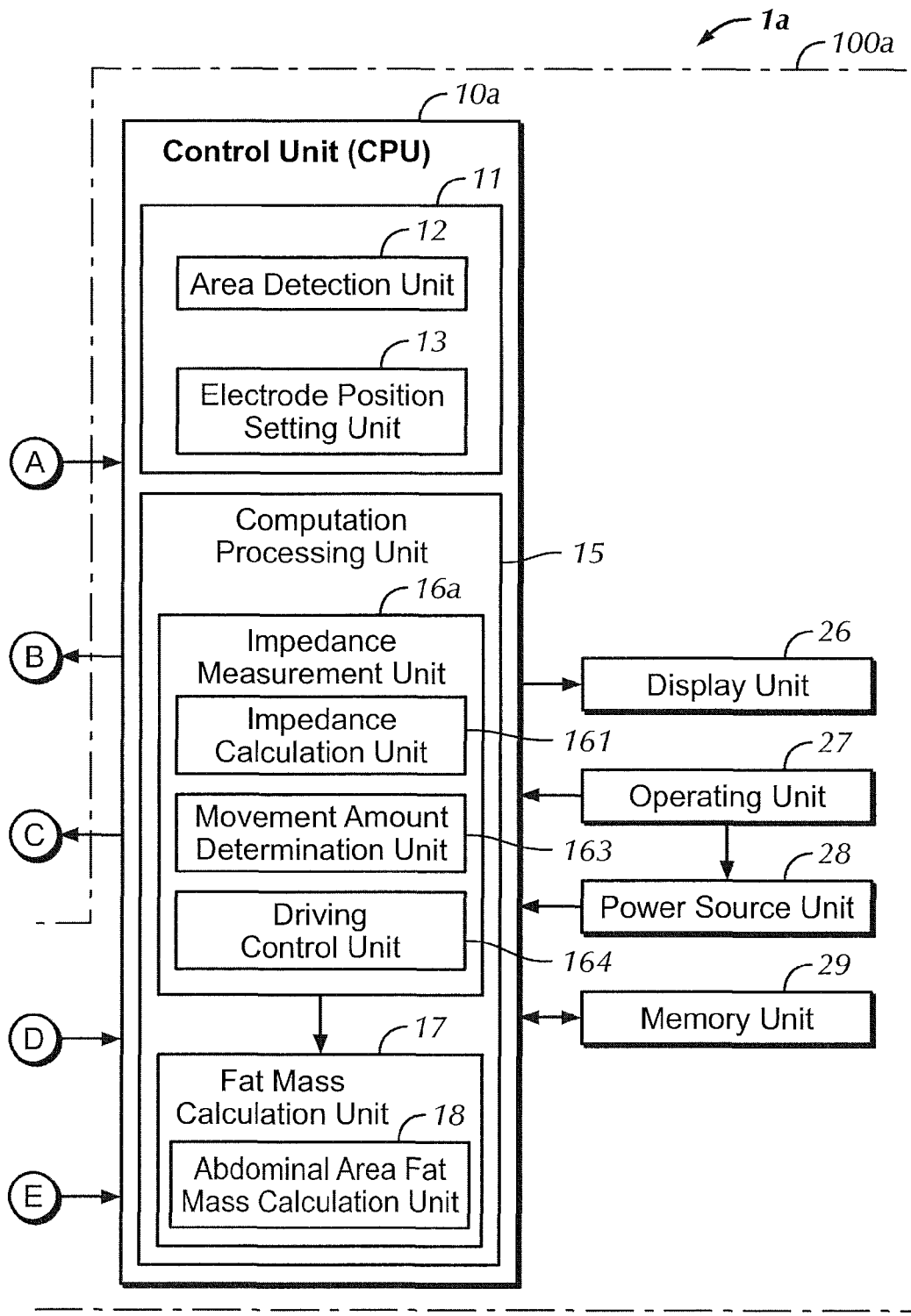

FIGS. 13A and 13B illustrate the functional configuration of the fat mass measurement apparatus 1A according to the second embodiment. The differences between the configuration of the fat mass measurement apparatus 1A shown in FIGS. 13A and 13B and the fat mass measurement apparatus 1 shown in FIGS. 3A and 3B are that the computer 100 and the control unit 101 have been replaced with the computer 100A and the control unit 101A.

The computer 100A includes a control unit 10A in place of the control unit 10 shown in FIG. 3B. Other configurations are the same as those of FIGS. 3A and 3B. The control unit 10A includes an impedance measurement unit 16A in place of the impedance measurement unit 16 shown in FIG. 3B. The impedance measurement unit 16A includes the impedance calculation unit 161, a movement amount determination unit 163, and a driving control unit 164. Other configurations of the control unit 10A are the same as those of the control unit 10.

The control unit 101A includes a slider control unit 34A for the frame member 110 in place of the slider control unit 34 for the slide bar 402 of the control unit 101. Other configurations of the control unit 101A are the same as those of the control unit 101.

The frame member slider control unit 34A includes a stepping motor for causing the frame member 110 to which the laser sensor 403 and the electrode support member 120 are attached to slide along the slide rail 300. The frame member 110 is connected to the rotating shaft of the stepping motor. When an instruction signal is inputted, the frame member slider control unit 34A rotates the stepping motor in accordance with a rotational amount specified by the instruction signal. Through this, the frame member 110 slides in tandem with the rotation of the stepping motor.

When the light-received signal is inputted from the laser sensor 403 via the sensor control unit 35 while the frame member 110 is sliding, the area detection unit 12 detects the rotational amount of the stepping motor in the frame member slider control unit 34A in response, and detects the position of the frame member 110 along the slide rail 300 based on the detected rotational amount. Through this, the positions of the marks 201 and 202 on the trunk area can be detected as corresponding positions on the slide rail 300. Then, based on the detected positions and the measurement subjects height information, the position of the abdominal area in the trunk area of the measurement subject who is lying face-up is calculated as a position along the slide rail 300 based on a predetermined conversion formula. Through this, the predetermined area with which the impedance measurement electrodes are to be brought into contact can be detected.

The electrode position setting unit 13 determines positions, on the surface of the body at the predetermined area detected by the area detection unit 12, with which the electrodes for measuring an impedance are to be brought into contact. In other words, as described earlier, detecting the position along the slide rail 300 that corresponds to the predetermined area in the trunk area of the measurement subject who is lying face-up makes it possible to calculate the vertical width of the predetermined area, or in other words, the length of the body axis direction, based on the detected position. Based on the calculated length of the predetermined area and the corresponding position of the predetermined area on the slide rail 300, the electrode position setting unit 13 calculates multiple positions on the predetermined area along the body axis direction as multiple corresponding positions on the slide rail 300. The multiple positions are calculated at each of predetermined intervals where an accurate measurement is to be obtained for the abdominal area fat volume. The calculated multiple positions are then set as positions with which the electrodes on the electrode support member 120 for impedance measurement are to be brought into contact. Here, to simplify the descriptions, it is assumed that the positions Pk through Pn shown in FIG. 5 have been set.

The movement amount determination unit 163 determines a relative movement amount from a reference position on the slide rail 300 (that is, a direction and distance at which the frame member 110 moves) for each of the multiple positions Pk through Pn on the slide rail 300 as set by the electrode position setting unit 13. The determined movement amount is then outputted to the driving control unit 164.

The driving control unit 164 determines, for each of the positions Pk through Pn, a rotational amount of the stepping motor based on the movement amounts corresponding to those positions. The driving control unit 164 then generates an instruction signal instructing the determined rotational amount and outputs that signal to the frame member slider control unit 34A. The frame member slider control unit 34A rotates the stepping motor in accordance with the rotational amount specified in the instruction signal. The frame member 110 slides in tandem with the rotation of the stepping motor. As a result, the electrode support member 120 can be moved, with the frame member 110, to each of the positions Pk through Pn set by the electrode position setting unit 13, and can be stopped at each of those positions.

Measurement Process

A measurement process performed by the fat mass measurement apparatus 1A according to the second embodiment will be described based on the flowcharts according to the first embodiment, illustrated in FIG. 6 in FIG. 7. Basically, the processing procedure is the same as in the first embodiment, and thus descriptions will focus on the processes that are different.

Referring to FIG. 6, the fat mass measurement apparatus 1A is inputted with various types of information (step S1), and the area detection unit 12 detects the position of the abdominal area in the trunk area of the measurement subject who is lying face-up as a position along the slide rail 300 based on the predetermined positions detected using the laser sensor 403 of the frame member 110 (step S3).

The electrode position setting unit 13 sets the positions Pk through Pn with which the impedance measurement electrodes are to be brought into contact as described above, based on the detected length of the predetermined area in the body axis direction (that is, the vertical width of the predetermined area) and the position of the predetermined area (step S5). When the input of a measurement instruction has been detected (YES in step S7) the movement amount determination unit 163 determines the movement amount as described above, in correspondence with each of the positions Pk through Pn determined in step S5.

First, the first position (the position Pk in FIG. 5) is selected (step S9). In other words, the movement amount determination unit 163 determines a movement amount corresponding to the first position, and outputs that movement amount to the driving control unit 164. The driving control unit 164 then generates an instruction signal based on the supplied movement amount and outputs that signal to the frame member slider control unit 34A. The stepping motor of the frame member slider control unit 34A rotates in accordance with the instruction signal. As a result, the frame member 110 slides to the first position and stops. At this time, the electrode pairs AP(1) to AP(4) on the electrode support member 120 are in contact with the surface of the body at the abdominal area.

After this, in the same manner as in the first embodiment, the impedance calculation unit 161 calculates an impedance in accordance with the flowchart shown in FIG. 7 at the first position (step S11), after which the abdominal area fat area Sv is calculated (step S13). When the abdominal area fat area Sv has been calculated at the first position, the next position (the position following the position Pk in FIG. 5) is selected (step S17), and in the same manner, the electrode support member 120 is moved to the next position and the abdominal area fat area Sv is calculated at the next position through the processes shown in steps S11 through S13. When the abdominal area fat area Sv has been calculated for all of the positions (the positions Pk through Pn in FIG. 5) by repeating such processing (YES in step S15), the abdominal area fat mass calculation unit 18 calculates the abdominal area fat volume based on Formula (1) (step S19). The calculated abdominal area fat volume is then displayed via the display unit 26 (step S21). This ends the abdominal area fat volume measurement.

In the present second embodiment, the laser sensor 403 is provided on the frame member 110, and thus the mechanism for moving the laser sensor 403 can also be employed as a mechanism for moving the electrodes, which makes it possible to miniaturize and simplify the apparatus.

Variations

The electrode mat 200 according to the first embodiment may be configured as a belt that is wrapped around the measurement subject's trunk area. In such a case, the impedances can be measured from the abdominal area front surface side through the measurement procedure described in the first embodiment by wrapping the belt so that the electrodes are positioned on the abdominal area front surface side.

The abdominal area fat volume may be measured by separately applying the measurement of the fat mass from the abdominal area rear surface according to the first embodiment and the measurement of the fat mass from the abdominal area front surface according to the second embodiment, or the measurement may be carried out using both measurements. In the case where both are used, the abdominal area fat mass calculation unit 18 calculates a visceral fat mass based on the impedances corresponding to both the abdominal area front surface and the abdominal area rear surface. Alternatively, the configuration may be such that the abdominal area fat mass calculation unit 18 calculates the abdominal area fat volume by selecting an impedance corresponding to one of the abdominal area front surface and the abdominal area rear surface. For example, the abdominal area fat mass calculation unit 18 may be configured so as to select the greater of the impedance corresponding to the abdominal area front surface and the impedance corresponding to the abdominal area rear surface.

Alternatively, the configuration may be such that the abdominal area fat mass calculation unit 18 selects the greater of an abdominal area fat volume based on a result of a measurement performed on the abdominal area front surface and an abdominal area fat volume based on a result of a measurement performed on the abdominal area rear surface.

Alternatively, the configuration may be such that the abdominal area fat mass calculation unit 18 calculates a representative value for the abdominal area fat volume based on a predetermined condition, such as finding the average value of an abdominal area fat volume based on a result of a measurement performed on the abdominal area front surface and an abdominal area fat volume based on a result of a measurement performed on the abdominal area rear surface and taking that average value as the representative value.

When measuring an abdominal area fat volume, it is necessary to change the contact positions of the impedance measurement electrodes in accordance with the measurement subject's body size, depending on whether the measurement subject has a large body or a small body; however, according to the aforementioned embodiments, the contact positions of the electrodes can be changed automatically in accordance with the body size. As a result, the electrodes can make contact at the proper positions for measuring the abdominal area fat volume, regardless of the measurement subject's body size, which makes it possible to calculate an accurate fat mass.

Meanwhile, unlike X-ray CT or MRI, oversized equipment is not necessary, and it is possible to calculate an accurate fat mass without taking time for geometrically calculating the fat mass from an image.

In addition, although a special bed such as that shown in FIG. 1 is prepared in the aforementioned embodiments, the invention is not limited thereto, and a typical commercial bed can also be used. In other words, an electrode mat 200 to which the slide rail 400 and the slider 401 are integrally attached is placed upon a commercial bed. In this case, the functionality of the control unit 101 shown in FIG. 1 is provided in the computer 100, and thus the electrode mat 200 on the commercial bed and the computer 100 communicate via a cable. Furthermore, although a comparatively large-size computer 100 is used in FIG. 1, a mobile, compact computer may be used in place of the computer 100.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

REFERENCE NUMERALS LIST 1,1A fat mass measurement apparatus
10,10A, 101,101A control unit
11 electrode determination unit
12 area detection unit
13 electrode position setting unit
15 computation processing unit
16, 16A impedance measurement unit
17 fat mass calculation unit
18 abdominal area fat mass calculation unit
24 body build information measurement unit
25 information input unit
26 display unit
27 operating unit
28 power source unit
29 memory unit
31 constant current generation unit
32 terminal switching unit
33 potential difference detection unit
34 slider control unit
34A frame member slider control unit
35 sensor control unit
40 cable
100, 100A computer
110 frame member
111 front frame portion
112 left frame portion
113 right frame portion
115 connection portion
120 electrode support member
121 front surface
161 impedance calculation unit
162 electrode selection unit
163 movement amount determination unit
164 driving control unit
200 electrode mat
201, 202 mark 291 coordinate table
292 correspondence relationship table
300, 400 slide rail
301, 401 slider
402 slide bar
403 laser sensor
404 mat
A11, A12, A13, A14, A21, A22, A23, A24 electrode
Sv abdominal area fat area

The invention claimed is:

1. A fat mass measurement apparatus for measuring a fat mass in a body based on a body impedance measured by bringing impedance measurement electrodes into contact with a measurement subject's body surface, the apparatus comprising:
    impedance measurement electrodes configured to come into contact with a measurement subject's body surface;
    an electrode support unit that supports said impedance measurement electrodes so as to be capable of making contact with the body surface;
    a position detection means for detecting a predetermined position in a trunk area of the measurement subject;
    an area detection means for detecting a predetermined area in the trunk area using the position detected by said position detection means;
    an electrode position setting means for setting, on the body surface at said predetermined area detected by said area detection means, a plurality of positions along a vertical direction of the trunk area for measuring said body impedance;
    a movement unit that moves said electrode support unit along said vertical direction of the trunk area;
    an impedance measurement means for measuring said body impedance by bringing said impedance measurement electrodes into contact with each of the plurality of positions set by said electrode position setting means,
        wherein said impedance measurement means comprises:
            a movement amount determination means for determining, for each of the plurality of positions on the body surface set by said electrode position setting means, a movement amount of said movement unit based on those positions; and
            a movement control means for controlling said movement unit based on the movement amounts for the plurality of positions determined by said movement amount determination means so as to move said electrode support unit to those positions; and
    a fat mass calculation means for calculating a fat mass of said predetermined area based on said body impedances at each of said plurality of positions measured by said impedance measurement means and a size of the trunk area at said predetermined area.

2. The fat mass measurement apparatus according to claim 1,
    wherein said fat mass calculation means calculates a fat volume of said predetermined area by calculating, for each of said plurality of positions, a fat area corresponding to those positions using a predetermined formula based on said body impedance and a circumferential length of the trunk area at said predetermined area, and integrating said calculated fat areas.

3. The fat mass measurement apparatus according to claim 1, further comprising:
    an electrode arrangement unit in which said plurality of impedance measurement electrodes are arranged so as to be capable of making contact with the body surface at an area of said body that includes at least said predetermined area,
    wherein said impedance measurement means comprises:
        an electrode selection means for selecting, based on each of the plurality of positions on the body surface set by said electrode position setting means, the impedance measurement electrodes to be brought into contact with those positions on the body surface, from among said plurality of impedance measurement electrodes arranged in said electrode arrangement unit.

4. The fat mass measurement apparatus according to claim 1,
    wherein said position detection means comprises:
        a mark detection means for detecting a mark, provided in relation to the body, for specifying said predetermined position, and
    wherein said predetermined position is detected based on an output of said mark detection means.

5. The fat mass measurement apparatus according to claim 1,
    wherein said position detection means further comprises:
        a sensor arrangement portion in which a plurality of pressure sensors capable of detecting a pressure resulting from a weight of an area of the body that includes said predetermined area are disposed, and
    wherein said predetermined area in the trunk area is detected based on detection signals from the plurality of pressure sensors in said sensor arrangement portion.

* * * * *